United States Patent [19]
St. Louis et al.

[11] Patent Number: 5,993,433
[45] Date of Patent: Nov. 30, 1999

[54] ABSORBENT ARTICLE WITH ENHANCED ELASTIC DESIGN FOR IMPROVED AESTHETICS AND CONTAINMENT

[75] Inventors: Raymond Gerard St. Louis, Fremont; David James VanEperen; Mark John Beitz, both of Appleton; Michael John Faulks, Neenah; Alan Francis Schleinz, Appleton; Daniel Robert Schlinz, Greenville, all of Wis.

[73] Assignee: Kimberly-Clark Worldwide, Inc., Neenah, Wis.

[21] Appl. No.: 08/954,400

[22] Filed: Oct. 20, 1997

[51] Int. Cl.⁶ .................................................. A61F 13/15
[52] U.S. Cl. ...................................... 604/385.2; 604/385.1
[58] Field of Search .............................. 604/385.2, 385.1, 604/386, 381, 382, 378

[56] References Cited

U.S. PATENT DOCUMENTS

| | | | |
|---|---|---|---|
| H1630 | 1/1997 | Roe et al. | 604/385.2 |
| 2,532,029 | 11/1950 | Medoff . | |
| 2,545,674 | 3/1951 | Ralph . | |

(List continued on next page.)

FOREIGN PATENT DOCUMENTS

| | | |
|---|---|---|
| 2130245 A1 | 4/1995 | Canada . |
| 2122700 A1 | 6/1995 | Canada . |
| 2130318 A1 | 9/1995 | Canada . |
| 2138428 A1 | 12/1995 | Canada . |

(List continued on next page.)

OTHER PUBLICATIONS

Federal Test Method Standard (FTMS) No. 191A, Method 5514, "Water Resistance of Cloth; Low Range, Hydrostatic Pressure Method," Jul. 20, 1978.
TAPPI Official Test Method T 543 om–94, "Bending Resistance of Paper (Gurley Type Tester)," published by the TAPPI Press, Atlanta, Ga., pp. 1–5.

*Primary Examiner*—Mark O. Polutta
*Attorney, Agent, or Firm*—Paul Yee

[57] ABSTRACT

An absorbent article (10) which includes a backsheet layer (30) having a pair of laterally opposed and longitudinally extending side margins (20). Each side margin has an outwardly concave, terminal side edge contour 15 located at appointed leg opening regions (17) in an intermediate portion (16) of the side margin. Each concave side edge contour (15) has a selected longitudinal extent along a length dimension (26) of the article (10). A liquid permeable topsheet layer (28) is connected in a superposed facing relation to the backsheet layer (30), and an absorbent body (32) is sandwiched between the topsheet layer (28) and the backsheet layer (30). A separately provided gusset-flap composite member (19) is connected to at least one of the backsheet and topsheet layers along each of the leg opening regions (17). The gusset-flap member (19) provides a leg gusset section (142) and a containment flap section (144). The gusset-flap member includes a barrier layer (174) having a pair of laterally opposed, longitudinally extending, barrier layer side edges (140, 141), and has a first major facing surface (148) and a second major facing surface (149). A nonwoven fabric layer (176) is joined in facing relation with the first facing surface (148) of the barrier layer (174). The fabric layer (176) has a leg gusset region (136), an outboard side portion (170), a containment flap region (63), and an inboard side portion (62). The outboard side portion (170) of the gusset-flap fabric layer (176) is arranged to wrap around at least one side edge of the barrier layer (174) and to extend inboard therefrom along the second facing surface (149) of the barrier layer (174). A first arrangement of a first plurality of separate, longitudinally extending elastomeric members (138) are attached and interposed between the barrier layer (174) and the fabric layer (176) within the leg gusset section (142) of the gusset-flap member (19).

25 Claims, 8 Drawing Sheets

U.S. PATENT DOCUMENTS

| | | |
|---|---|---|
| 2,575,163 | 11/1951 | Donovan . |
| 2,575,164 | 11/1951 | Donovan . |
| 2,893,393 | 7/1959 | Pressley . |
| 2,956,564 | 10/1960 | Ohara . |
| 3,386,442 | 6/1968 | Sabee . |
| 3,901,236 | 8/1975 | Assarsson et al. . |
| 4,076,663 | 2/1978 | Masuda et al. ............... 260/17.4 GC |
| 4,286,082 | 8/1981 | Tsubakimoto et al. ................ 526/240 |
| 4,381,781 | 5/1983 | Sciaraffa et al. ....................... 604/372 |
| 4,585,448 | 4/1986 | Enloe ..................................... 604/378 |
| 4,636,207 | 1/1987 | Buell ...................................... 604/370 |
| 4,643,728 | 2/1987 | Karami ............................... 604/385 A |
| 4,657,539 | 4/1987 | Hasse .................................. 604/385 A |
| 4,662,877 | 5/1987 | Williams ............................. 604/385 A |
| 4,663,220 | 5/1987 | Wisneski et al. ...................... 428/221 |
| 4,681,579 | 7/1987 | Toussant et al. .................... 604/385 R |
| 4,695,278 | 9/1987 | Lawson ............................... 604/385 A |
| 4,699,823 | 10/1987 | Kellenberger et al. ................ 428/219 |
| 4,704,116 | 11/1987 | Enloe .................................. 604/385 A |
| 4,738,677 | 4/1988 | Foreman .............................. 607/385.2 |
| 4,743,246 | 5/1988 | Lawson ................................ 604/385.2 |
| 4,753,646 | 6/1988 | Enloe .................................. 604/385 R |
| 4,770,656 | 9/1988 | Proxmire et al. ...................... 604/393 |
| 4,795,454 | 1/1989 | Dragoo ................................. 604/385.2 |
| 4,808,177 | 2/1989 | DesMarais et al. ................. 604/385.1 |
| 4,816,025 | 3/1989 | Foreman .............................. 604/385.2 |
| 4,822,435 | 4/1989 | Igaue et al. ............................ 156/164 |
| 4,834,740 | 5/1989 | Suzuki et al. ......................... 604/385.2 |
| 4,846,823 | 7/1989 | Enloe ................................... 604/385.2 |
| 4,846,825 | 7/1989 | Enloe et al. .......................... 604/385.1 |
| 4,861,652 | 8/1989 | Lippert et al. .......................... 428/284 |
| 4,883,480 | 11/1989 | Huffman et al. ..................... 604/385.1 |
| 4,892,528 | 1/1990 | Suzuki et al. ......................... 604/385.2 |
| 4,904,251 | 2/1990 | Igaue et al. ........................... 604/385.2 |
| 4,916,005 | 4/1990 | Lippert et al. .......................... 428/192 |
| 4,938,754 | 7/1990 | Mesek .................................. 604/385.2 |
| 4,938,755 | 7/1990 | Foreman .............................. 604/385.2 |
| 4,949,668 | 8/1990 | Heindel et al. ......................... 118/314 |
| 4,998,929 | 3/1991 | Bjorksund et al. ................... 604/385.2 |
| 5,019,066 | 5/1991 | Freeland et al. ..................... 604/385.2 |
| 5,021,051 | 6/1991 | Hiuke ................................... 604/385.2 |
| 5,026,364 | 6/1991 | Robertson ............................ 604/385.1 |
| 5,028,224 | 7/1991 | Pieper et al. ............................ 425/80.1 |
| 5,032,120 | 7/1991 | Freeland et al. ..................... 604/385.2 |
| 5,061,261 | 10/1991 | Suzuki et al. ......................... 604/385.2 |
| 5,064,489 | 11/1991 | Ujimoto et al. ........................ 156/164 |
| 5,080,658 | 1/1992 | Igaue et al. ........................... 604/385.2 |
| 5,085,654 | 2/1992 | Buell ...................................... 604/370 |
| 5,087,255 | 2/1992 | Sims ..................................... 604/385.1 |
| 5,114,420 | 5/1992 | Igaue et al. ........................... 604/385.2 |
| 5,137,526 | 8/1992 | Coates ................................... 604/391 |
| 5,147,343 | 9/1992 | Kellenberger ........................... 604/368 |
| 5,167,653 | 12/1992 | Igaue et al. ........................... 604/385.2 |
| 5,176,672 | 1/1993 | Bruemmer et al. .................. 604/385.1 |
| 5,188,627 | 2/1993 | Igaue et al. ........................... 604/385.2 |
| 5,221,277 | 6/1993 | Beplate ................................... 604/394 |
| 5,226,992 | 7/1993 | Morman ................................. 156/62.4 |
| 5,246,432 | 9/1993 | Suzuki et al. ......................... 604/385.2 |
| 5,275,590 | 1/1994 | Huffman et al. ..................... 604/385.2 |
| 5,292,316 | 3/1994 | Suzuki .................................. 604/385.2 |
| 5,304,159 | 4/1994 | Tanji et al. ............................ 604/385.2 |
| 5,304,160 | 4/1994 | Igaue et al. ........................... 604/385.2 |
| 5,308,344 | 5/1994 | Toth ...................................... 604/378 |
| 5,330,598 | 7/1994 | Erdman et al. ......................... 156/164 |
| 5,340,648 | 8/1994 | Rollins et al. ........................... 428/343 |
| 5,342,342 | 8/1994 | Kitaoka ................................ 604/385.2 |
| 5,344,516 | 9/1994 | Tanji et al. ............................. 156/164 |
| 5,360,422 | 11/1994 | Brownlee et al. .................... 604/385.2 |
| 5,368,584 | 11/1994 | Clear et al. ........................... 604/385.2 |
| 5,397,318 | 3/1995 | Dreier .................................. 604/385.2 |
| 5,399,219 | 3/1995 | Roessler et al. ......................... 156/259 |
| 5,407,438 | 4/1995 | Hedlund et al. ..................... 604/385.2 |
| 5,409,476 | 4/1995 | Coates ................................... 604/391 |
| 5,417,680 | 5/1995 | Kimura et al. ....................... 604/385.2 |
| 5,451,219 | 9/1995 | Suzuki et al. ......................... 604/385.2 |
| 5,454,803 | 10/1995 | Sageser et al. ....................... 604/385.2 |
| 5,476,458 | 12/1995 | Glaug et al. ............................ 604/378 |
| 5,486,166 | 1/1996 | Bishop et al. .......................... 604/366 |
| 5,489,282 | 2/1996 | Zehner et al. ....................... 604/385.1 |
| 5,490,846 | 2/1996 | Ellis et al. .............................. 604/366 |
| 5,501,756 | 3/1996 | Rollins et al. ........................... 156/167 |
| 5,507,909 | 4/1996 | Rollins et al. ........................... 156/425 |
| 5,527,300 | 6/1996 | Sauer .................................... 604/378 |
| 5,527,302 | 6/1996 | Endres et al. ........................ 604/385.1 |
| 5,531,730 | 7/1996 | Dreier .................................. 604/385.2 |
| 5,540,671 | 7/1996 | Dreier .................................. 604/385.2 |
| 5,540,672 | 7/1996 | Roessler et al. ..................... 604/385.2 |
| 5,540,796 | 7/1996 | Fries ..................................... 156/164 |
| 5,542,943 | 8/1996 | Sageser ................................ 604/385.2 |
| 5,549,592 | 8/1996 | Fries et al. ............................. 604/389 |
| 5,554,142 | 9/1996 | Dreier et al. ......................... 604/385.1 |
| 5,558,660 | 9/1996 | Dreier .................................. 604/385.2 |
| 5,558,661 | 9/1996 | Roe et al. ............................. 604/385.2 |
| 5,562,650 | 10/1996 | Everett et al. .......................... 604/378 |
| 5,565,050 | 10/1996 | Sageser et al. ........................ 156/73.1 |
| 5,567,254 | 10/1996 | Sageser ................................. 156/73.1 |
| 5,569,227 | 10/1996 | Vendermoortele ................... 604/385.1 |
| 5,571,096 | 11/1996 | Dobrin et al. .......................... 604/383 |
| 5,575,785 | 11/1996 | Gryskiewicz et al. ............... 604/385.2 |
| 5,576,091 | 11/1996 | Zajaczkowski et al. ................ 428/192 |
| 5,577,540 | 11/1996 | Sageser ................................. 156/226 |
| 5,582,606 | 12/1996 | Bruemmer et al. .................. 604/385.2 |
| 5,584,828 | 12/1996 | Yamamoto et al. ................. 607/385.2 |
| 5,593,401 | 1/1997 | Sosalla et al. ........................ 604/385.2 |
| 5,595,618 | 1/1997 | Fries et al. ............................. 156/164 |
| 5,599,338 | 2/1997 | Enloe ................................... 604/385.2 |
| 5,599,417 | 2/1997 | Glaug et al. ............................ 156/227 |
| 5,601,543 | 2/1997 | Dreier et al. ......................... 604/385.1 |
| 5,601,544 | 2/1997 | Glaug et al. .......................... 604/385.2 |
| 5,601,546 | 2/1997 | Tanji et al. ........................... 604/385.2 |
| 5,605,735 | 2/1997 | Zehner et al. .......................... 428/100 |
| 5,624,426 | 4/1997 | Roe et al. ............................. 601/385.2 |
| 5,628,737 | 5/1997 | Dobrin et al. .......................... 604/383 |
| 5,824,172 | 10/1998 | Kielpikowski ....................... 604/385.2 |
| 5,827,259 | 10/1998 | Levy et al. ............................ 607/385.2 |

FOREIGN PATENT DOCUMENTS

| | | | |
|---|---|---|---|
| 0 217 032 A3 | 4/1987 | European Pat. Off. . | |
| 0 243 013 A1 | 10/1987 | European Pat. Off. . | |
| 0 251 332 B1 | 1/1988 | European Pat. Off. . | |
| 0 312 071 A2 | 4/1989 | European Pat. Off. . | |
| 0 324 133 B1 | 7/1989 | European Pat. Off. . | |
| 0 329 160 B1 | 8/1989 | European Pat. Off. . | |
| 0 339 461 B1 | 11/1989 | European Pat. Off. . | |
| 0 346 477 B1 | 12/1989 | European Pat. Off. . | |
| 0 376 022 B1 | 7/1990 | European Pat. Off. . | |
| 0 386 815 A2 | 9/1990 | European Pat. Off. . | |
| 0 403 832 B1 | 12/1990 | European Pat. Off. . | |
| 0 404 648 B1 | 12/1990 | European Pat. Off. ........ | A61F 13/15 |
| 0 433 951 A2 | 6/1991 | European Pat. Off. . | |
| 433951 | 6/1991 | European Pat. Off. . | |
| 0 532 035 A3 | 3/1993 | European Pat. Off. . | |
| 0 568 085 A1 | 11/1993 | European Pat. Off. . | |
| 0 593 082 A1 | 4/1994 | European Pat. Off. . | |
| 0 622 063 A3 | 11/1994 | European Pat. Off. . | |
| 0 664 997 A1 | 8/1995 | European Pat. Off. . | |
| 0 678 289 A1 | 10/1995 | European Pat. Off. . | |
| 0 678 290 A1 | 10/1995 | European Pat. Off. . | |
| 0 745 367 A2 | 12/1996 | European Pat. Off. . | |
| 0 750 894 A2 | 1/1997 | European Pat. Off. . | |
| 0 750 895 A2 | 1/1997 | European Pat. Off. . | |
| 2677541 A1 | 12/1992 | France . | |

FOREIGN PATENT DOCUMENTS

| | | |
|---|---|---|
| 7-184954 | 7/1995 | Japan . |
| 7-184955 | 7/1995 | Japan . |
| 92/4165 | 6/1992 | South Africa . |
| 92/6027 | 8/1992 | South Africa . |
| 2159693 | 12/1985 | United Kingdom . |
| 2216393 | 10/1989 | United Kingdom . |
| 2265550 | 6/1993 | United Kingdom . |
| 2262873 | 7/1993 | United Kingdom . |
| 2265834 | 10/1993 | United Kingdom . |
| 2266055 | 10/1993 | United Kingdom . |
| 2266225 | 10/1993 | United Kingdom . |
| 2266444 | 11/1993 | United Kingdom . |
| 2268389 | 1/1994 | United Kingdom . |
| 2270247 | 3/1994 | United Kingdom . |
| 2271501 | 4/1994 | United Kingdom . |
| 2275610 | 9/1994 | United Kingdom . |
| 2275611 | 9/1994 | United Kingdom . |
| 2278993 | 12/1994 | United Kingdom . |
| 2280374 | 2/1995 | United Kingdom . |
| 2283663 | 5/1995 | United Kingdom . |
| 2284538 | 6/1995 | United Kingdom . |
| 2285409 | 7/1995 | United Kingdom . |
| 2288540 | 10/1995 | United Kingdom . |
| WO 91/08717 A1 | 6/1991 | WIPO . |
| WO 92/07533 A1 | 5/1992 | WIPO . |
| WO 92/09253 A1 | 6/1992 | WIPO . |
| WO 92/12648 A1 | 8/1992 | WIPO . |
| WO 92/22271 A1 | 12/1992 | WIPO . |
| WO 93/00059 A1 | 1/1993 | WIPO ............................. A61F 13/15 |
| WO 93/03698 A1 | 3/1993 | WIPO ............................. A61F 13/15 |
| WO 93/09739 A1 | 3/1993 | WIPO ............................. A61F 13/15 |
| WO 93/05742 A1 | 4/1993 | WIPO . |
| WO 93/05744 A1 | 4/1993 | WIPO . |
| WO 93/12746 A1 | 7/1993 | WIPO . |
| WO 93/23000 A1 | 11/1993 | WIPO . |
| WO 94/10951 A1 | 5/1994 | WIPO . |
| WO 94/14395 A1 | 7/1994 | WIPO . |
| WO 94/18927 A1 | 9/1994 | WIPO . |
| WO 94/28840 A2 | 12/1994 | WIPO . |
| WO 95/07063 A1 | 3/1995 | WIPO ............................. A61F 13/15 |
| WO 95/14453 A2 | 6/1995 | WIPO . |
| WO 95/16417 A1 | 6/1995 | WIPO . |
| WO 95/22951 A1 | 8/1995 | WIPO . |
| WO 95/25493 A1 | 9/1995 | WIPO . |
| WO 95/25494 A1 | 9/1995 | WIPO . |
| WO 95/32699 A1 | 12/1995 | WIPO . |
| WO 96/05788 A1 | 2/1996 | WIPO ............................. A61F 13/15 |
| WO 96/05792 A1 | 2/1996 | WIPO . |
| WO 96/09025 A1 | 3/1996 | WIPO . |
| WO 96/24320 A1 | 8/1996 | WIPO . |
| WO 96/31176 A1 | 10/1996 | WIPO . |
| WO 97/09016 A1 | 3/1997 | WIPO . |
| WO 97/12571 A1 | 4/1997 | WIPO . |
| WO 97/20532 A1 | 6/1997 | WIPO . |

# ABSORBENT ARTICLE WITH ENHANCED ELASTIC DESIGN FOR IMPROVED AESTHETICS AND CONTAINMENT

FIELD OF THE INVENTION

The present invention relates to an article having one or more elasticized, peripheral margins. More particularly, the invention relates to an article which incorporates a distinctively elasticized containment system at legband and/or waistband portions of the article.

BACKGROUND OF THE INVENTION

Conventional absorbent articles, such as disposable diapers, have been constructed with various types of elasticized waistbands and elasticized leg bands or leg cuffs. Such article designs have also included additional, elasticized containment or barrier flaps at the leg and/or waist sections of the article. Particular article designs have incorporated a stretchable outer cover composed of an elastomeric web material, such as a stretch-bonded laminate which includes a layer of nonwoven fabric. Other conventional designs have included separate elastomeric or nonelastomeric side panel members connected to the lateral side edges of a backsheet or outercover member, and have included fastening systems and fastening tabs connected to the side panels for securing the article on a wearer.

Articles which incorporate conventional elasticized margins and conventional barrier flap configurations at their legband sections have, however, exhibited various shortcomings. For example, it has been difficult to avoid red marking of the wearer's skin and difficult to maintain the desired operation of the barrier flaps when the articles are being worn. Even when the barrier flaps are constructed of an elastomeric material or otherwise elasticized, it has been difficult to maintain contact between the movable edge of the barrier flap and the wearer's body and has been difficult to reliably hold the flap open for an effective receipt and containment of urine and feces. As a result, there has been a continued need for improved containment structures at the leg regions of the absorbent articles.

BRIEF DESCRIPTION OF THE INVENTION

The present invention can provide a distinctive article which includes a backsheet layer having a pair of laterally opposed side margins, with each side margin having a terminal side edge contour located at an appointed leg opening region in each of the side margins. A liquid permeable topsheet layer is connected in superposed relation to the backsheet layer, and an absorbent body is positioned and held between the topsheet layer and the backsheet layer. A separate, elasticized gusset-flap member is connected to the article along each of the appointed leg opening regions, and each gusset-flap member has a leg gusset section and a containment flap section. The leg gusset section is configured to extend beyond and to bridge between opposed, spaced-apart portions of an associated one of the side edge contours of the backsheet layer.

In particular aspects, the absorbent article can include a backsheet layer having a pair of laterally opposed and longitudinally extending side margins, with each side margin having an outwardly concave, terminal side edge contour located at appointed leg opening regions in an intermediate portion of the side margin. Each concave side edge contour has a selected longitudinal extent along a length dimension of the article. A liquid permeable topsheet layer is connected in a superposed facing relation to the backsheet layer, and an absorbent body is sandwiched between the topsheet layer and the backsheet layer. A separately provided gusset-flap composite member is connected to at least one of the backsheet and topsheet layers along each of the leg opening regions. The gusset-flap member provides a leg gusset section and a containment flap section. The gusset-flap member includes a barrier layer having a pair of laterally opposed, longitudinally extending, barrier layer side edges, and the barrier layer has a first major surface and a second major surface. A nonwoven fabric layer is joined in facing relation with the first surface of the barrier layer, and the fabric layer has a leg gusset region, an outboard side portion, a containment flap region, and an inboard side portion. The outboard side portion of the gusset-flap fabric layer is arranged to wrap around at least one side edge of the barrier layer and to extend inboard therefrom along the second surface of the barrier layer. A first arrangement of a first plurality of separate, longitudinally extending elastomeric members are attached and interposed between the barrier layer and the fabric layer within the leg gusset section of the gusset-flap member.

The configurations and arrangements of the various aspects of the invention can provide an article having a gentle, soft, and more conformable leg gather, and can provide a barrier flap structure that can more reliably and more effectively maintain an open position when the associated absorbent article is being worn. In addition, the open flap configuration can be sustained while avoiding excessive irritation of the wearer's skin. The resultant article can exhibit less gapping at the leg opening regions, and can provide a more cushioning operation and appearance. The article can also provide a leg gather which may move more independently from the main portion of the absorbent article to provide a leg gather more conformable to the leg. In addition, the article can provide leg gusset and containment flap configurations which provides a more tortuous path for better resisting the leakage of any free liquids in the absorbent article. The arrangements of the constituent components and the combination of operational parameters, such as the controlled stiffness and the controlled articulation of the barrier flap, can advantageously provide an improved absorbent structure which can have less leakage, and can afford increased comfort to the wearer.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

Figure 1:
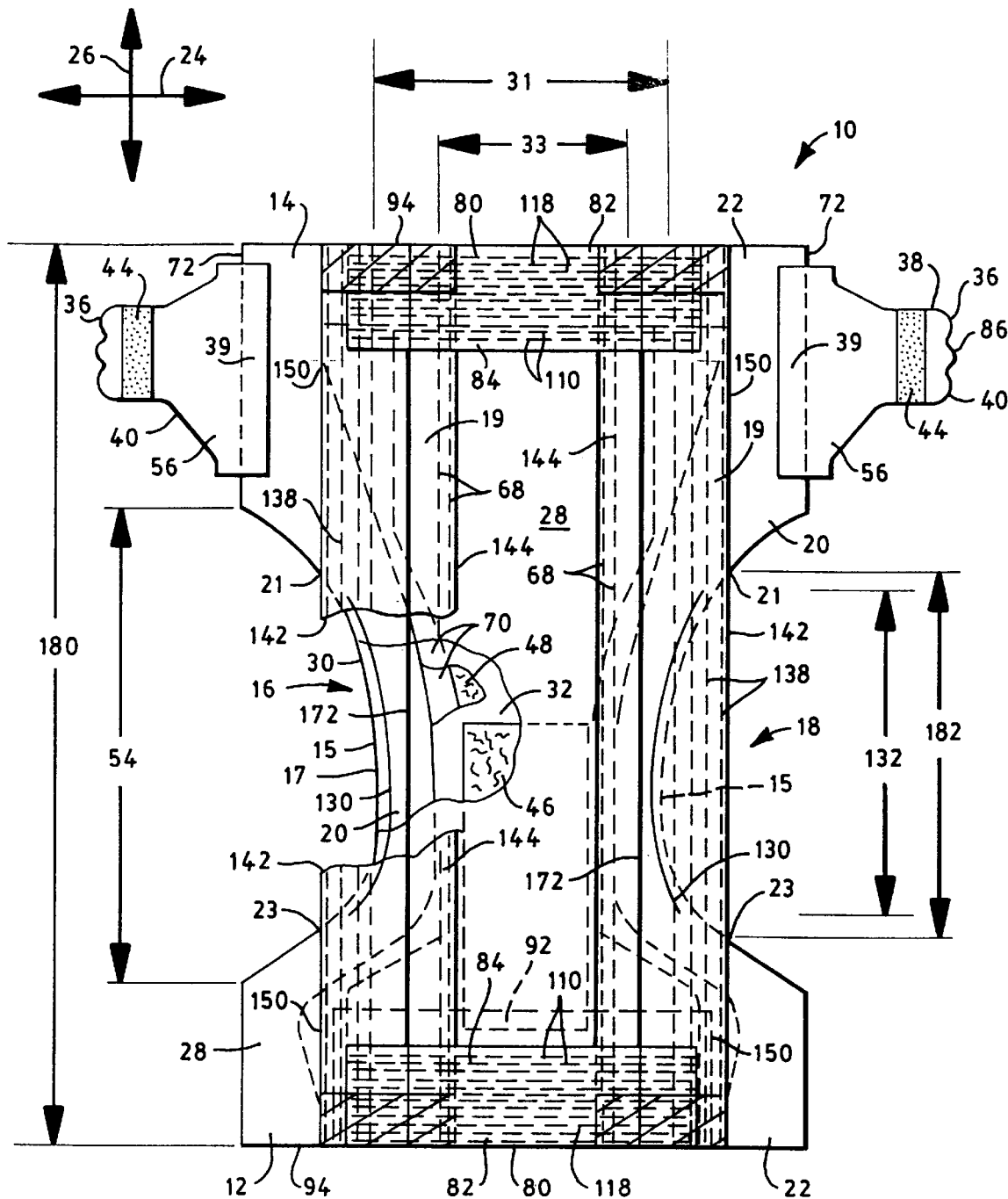
FIG. 1 representatively shows a partially cut-away, top view of an article of the invention.

The present invention will be described herein in relationship to producing an elasticized containment system for absorbent articles, particularly disposable absorbent articles. The articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

In addition, the invention will be described in the context of its various configurations and aspects. It should be appreciated that alternative arrangements of the invention can comprise any combination which includes one or more of the various configurations and aspects of the invention.

With reference to FIGS. 1, 2, 3 and 4, a representative article, such as a diaper 10, includes a front waistband portion 12, a back waistband portion 14, an intermediate portion 16 which interconnects the front and back waistband portions, and a pair of laterally opposed side margins 20. Extending along the side margins 20 are integrally formed gusset-flap members 19 which include a containment flap region 144 and a leg gusset region 142. The article has a backsheet layer 30, and a liquid permeable topsheet layer 28 connected in superposed relation to the backsheet layer. An absorbent body structure 32 is sandwiched between the topsheet layer and the backsheet layer, and an elastomeric component, such as an elasticized, waist pocket member 80, may optionally be connected to at least one of the backsheet and topsheet layers along at least one end margin 22 of the article.

The representatively shown article includes a pair of longitudinally opposed end margins 22, and a pair of laterally opposed elasticized side margins 20. The elasticized, waist pocket member 80 is connected and attached to at least one of the backsheet and topsheet layers along at least one end margin 22 of the article. The shown waist pocket member 80 includes an extending flange section 82 and an extending pocket section 84. The pocket section 84 of the waist pocket/flap member 80 includes a substantially fixed edge portion 102 secured to the article, and includes an elasticized, gathered moveable edge portion 104 which is longitudinally spaced from the fixed edge portion 102. The pocket section also includes a substantially liquid impermeable pocket barrier layer 106, and a pocket fabric layer 108 connected in a laminated, facing relation with the pocket barrier layer. A plurality of separate, laterally extending pocket elastic members 110 are sandwiched between the pocket barrier layer 106 and the pocket fabric layer 108 to provide an elasticized waist pocket composite 112 which is substantially laterally gathered.

A fastening system 40 is operably connected and joined to the article at either or both of the laterally opposed end regions 72 of at least one of the front and rear waistband sections, such as the illustrated rear waistband 14. A cooperating side panel member 56 can be associated with each fastening system and may be constructed to be nonelasticized, or may be constructed to be elastomerically stretchable at least along the laterally extending cross-direction 24 of the article. In addition, a fastening tab 36 can be attached to extend laterally outboard from each side panel member 56. In a particular aspect of the invention, the representatively shown diaper article can have a cross-wise, lateral dimension 24, a length-wise, longitudinal dimension 26, laterally opposed side margins and longitudinally opposed end margins. The article provides a front waistband portion 12, a rear or back waistband portion 14, and an intermediate portion 16 which interconnects the front and rear waistband portions. The article includes a backsheet layer 30 having a pair of laterally opposed and longitudinally extending side margins 20. Each side margin has an outwardly concave, terminal side edge contour 15 located at appointed leg opening regions 17 in an intermediate portion 16 of each of the side margins. Each concave side edge contour 15 has a selected longitudinal extent 54 along a length dimension 26 of the article 10. A porous, liquid permeable topsheet layer 28 has a laterally extending width and a longitudinally extending length, and is connected in superposed relation to the backsheet layer 30. An absorbent body structure 32, is sandwiched and operably secured between the backsheet layer 30 and the topsheet layer 28. A separately provided gusset-flap composite member 19 is connected to at least one of the backsheet and topsheet layers along each of the leg opening regions 17. The gusset-flap member 19 provides a leg gusset section 142 and a containment flap section 144. Each leg gusset section 142 is configured to extend beyond and bridge across its corresponding, outwardly concave terminal side edge contour 15 of the backsheet layer 30, and is configured to provide an elasticized and gathered side margin of the article. Each containment flap section 144 is integrally formed with a corresponding one of the leg gusset sections 142 and is positioned relatively inboard therefrom to provide the gusset-flap member 19. Each containment flap section 144 has a substantially fixed edge 64 located proximally adjacent to a one of the elasticized side margins 20, and has a elasticized and gathered, distal, movable edge portion 66. The gusset-flap member 19 includes a barrier layer 174 having a pair of laterally opposed, longitudinally extending barrier layer side edges 140 and 141, and has a first major facing surface 148 and a second major facing surface 149. A gusset-flap fabric layer 176 may be composed of a nonwoven fabric, and is desirably positioned and joined in an immediate, facing relation with the first facing surface 148 of the gusset-flap barrier layer 174. The fabric layer 176 includes a leg gusset region 136, an outboard side portion 170 of the leg gusset region, a containment flap region 63, and an inboard side portion 62 of the containment flap region. The outboard side portion 170 of the fabric layer 176 is arranged to wrap around at least one side edge of the barrier layer 174 and to extend inboard therefrom along the second facing surface 149 of the barrier layer. A first arrangement of a first plurality of separate, longitudinally extending elastomeric members 138 is attached and sandwiched by the barrier layer 174 and the fabric layer 176 within the leg gusset section 142 of the gusset flap member 19. A second arrangement of at least one longitudinally extending elastomeric member 68 is attached to at least the fabric layer 176 within each containment flap section 144 of the gusset-flap member 19. The first and second arrangements of elastomeric members 138 and 68 can thereby provide an elastomeric, substantially longitudinally gathered, gusset-flap composite member 19.

The leg gusset section 142 of each gusset-flap 19 is configured to extend beyond and past the concave side edge contours 15 of the backsheet layer 30 to provide an elasticized leg cuff in at least the intermediate portion of the article. Additionally, each gusset section 142 is configured to bridge between opposed, spaced-apart portions 21 and 23 of an associated one of the concave side edge contours 15 of the backsheet layer 30. In particular, each leg gusset section is configured to extend beyond and to bridge between opposed spaced-apart portions 21 and 23 to thereby span across a "mouth" of a generally C-shaped gap formed by the terminal edge of its corresponding side edge contour 15. Each gusset-flap member 19 may be operably attached to the inward, bodyside surface of the topsheet 28.

The various configurations of the invention can include two or more cooperating gusset-flaps 19, such as the shown laterally opposed pair of gusset-flaps. With respect to each other, the gusset-flaps can be arranged to be parallel or non-parallel to each other, and each individual gusset-flap can be straight and/or curvilinear.

In a particular aspect of the invention, the inboard side portion 62 of the gusset-flap fabric layer 176 is arranged to fold and wrap around an appointed folding line or other region. The resultant, folded over portion can then be arranged to operatively sandwich or otherwise enclose the second arrangement 68 of at least one longitudinally extending elastomeric member.

In another aspect of the invention, the barrier layer 174 can be configured to extend into the containment flap section 144 of the gusset-flap 19, and the inboard side portion 62 of the gusset-flap fabric layer 176 can be arranged to wrap around the second side edge 141 of the barrier layer 174 to extend along the second major surface 149 of the barrier layer. In addition, the second set 68 of the at least one longitudinally extending elastomeric member can be attached between the containment flap region 63 of the fabric layer 176 and a containment flap region 61 of the barrier layer 174 within the containment flap section 144 of each gusset flap member 19.

Further aspects of the invention can provide an absorbent article in which the backsheet layer 30 may include a crotch region thereof having a crotch width 31 which is particularly narrow. In particular aspects the crotch width of the backsheet layer can be up to about 240 mm. Desirably the crotch width of the backsheet layer can be not more than a maximum of about 160 mm. Other aspects of the invention can provide an article in which the absorbent body 32 is constructed with a crotch width thereof which is also quite narrow. Desirably the crotch region of the absorbent body can have a crotch width 33 which can be not more than about 102 mm, and optionally is not more than about 76 mm, and in addition, the crotch width of the absorbent body can be at least about 25 percent (%) of the width of the backsheet layer 30 in the crotch region of the article. In still other aspects of the invention, each separate, elasticized and gathered gusset-flap 19 can be connected to at least one of the topsheet and backsheet layers with a gusset attachment 172 which extends along each of the appointed leg opening regions. Each gusset attachment 172 can be spaced from an associated, proximally adjacent, longitudinally extending side edge of the absorbent body 32 by a gusset spacing distance of not more than about 51 mm. Alternatively, the gusset spacing distance can be not more than about 25 mm, and optionally, can be not more than about 13 mm, at least when measured within the crotch region 18 of the article. The various aspects and configurations of the invention can provide distinctive combinations of softness, body conformity, reduced bunching between the wearer's legs, reduced red-marking of the wearer's skin, and improved leakage protection.

FIG. 1 is a representative, top plan view of diaper 10 of the present invention in its flatout, uncontracted state (i.e., with all elastic induced gathering and contraction removed). Portions of the structure are partially cut away to more clearly show the interior construction of diaper 10, and the surface of the diaper which contacts the wearer is facing the viewer. The outer edges of the diaper define a periphery in which the longitudinally extending side edge margins are designated 20 and the laterally extending end edge margins are designated 22. The side edges define leg openings for the diaper, and optionally, are curvilinear and contoured. The end edges are shown as straight, but optionally, may be curvilinear.

Diaper 10 typically includes a porous, liquid permeable topsheet 28; a substantially liquid impermeable backsheet 30; an absorbent structure 32, positioned and connected between the topsheet and backsheet; a surge management portion 46; and elastomeric members for elasticizing the diaper margins at the legband and waistband regions. The surge management portion is positioned in liquid communication with the absorbent structure, and the absorbent structure includes a retention portion 48. The topsheet 28, backsheet 30, absorbent structure 32, surge management portion 46 and the elastic members may be assembled in a variety of well-known diaper configurations. In addition, the diaper can include a system of relatively inboard barrier flaps, such as containment flap sections 144, positioned proximally adjacent to the diaper legbands.

As representatively shown, the topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery of diaper 10. The waistband regions comprise those upper portions of diaper 10, which when worn, wholly or partially cover or encircle the waist or mid-lower torso of the wearer. The intermediate, region 16 lies between and interconnects waistband regions 12 and 14, and includes a crotch region 18 which comprises that portion of diaper 10 which, when worn, is positioned between the legs of the wearer and covers the lower torso of the wearer. Thus, the crotch region 18 is an area where repeated fluid surges typically occur in the diaper or other disposable absorbent article. The topsheet 28 presents a body-facing surface which is compliant, soft-feeling, and non-irritating to the wearer's skin. Further, the topsheet 28 can be less hydrophilic than retention portion 48, and is sufficiently porous to be liquid permeable, permitting liquid to penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 20 gsm (g/m$^2$) and density of about 0.13 gm/cc. The fabric can be surface treated with a selected amount of surfactant, such as about 0.28% TRITON X-102 surfactant available from Union Carbide, a business having offices in Danbury, Conn. The surfactant can be applied by any conventional means, such as spraying, printing, brush coating or the like.

The surfactant material, such as a conventional wetting agent, can be applied to a medial section of the topsheet layer 28 to provide a greater wettability of the medial section, as compared to a remainder of the topsheet layer 28. In particular configurations, the cross-directional width of the medial section can be substantially equal to or less than the cross-directional width of the surge management portion 46. In alternative configurations, the medial section width can be substantially equal to or less than a cross-directional spacing between a pair of adhesive strips or other bonds employed to secure the containment flap sections 144 onto topsheet 28 and to form a leak resistant barrier seal onto the backsheet 30.

The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

In the various configurations of the invention, the fabric layer employed in the gusset-flap members 19 and/or the waist flaps 84, may, for example, be constructed of a fibrous material which is similar to the material comprising topsheet 28, or similar to the material comprising surge management portion 46. Examples of these materials include but are not limited to spunbond, spunbond-meltblown-spunbond (SMS) laminated, meltblown, spunbond-meltblown laminated, spunlaced, thermal point bonded carded web, through-air bonded carded web, coform, and hydroknit materials. Other conventional materials, such as polymer films, may also be incorporated into such barrier flap components. In particular aspects of the invention, the barrier flap components can be constructed of a material which is permeable only to gas, such as ambient air. Alternative configurations of the invention can include barrier flaps which are constructed of a material which is resistant to a passage of aqueous liquid, such as urine, therethrough. For example, the barrier flap sections of the gusset-flap members may include a fabric layer which is constructed of a spunbond-meltblown-spunbond (SMS) laminate material. For example, the barrier flap sections of the gusset-flap members can be constructed of a SMS material having a basis weight of about 0.60–0.75 oz/yd$^2$ (about 20–25 g/m$^2$). The spunbond layers can composed of polypropylene fibers, and the meltblown layer can be composed of meltblown polypropylene fibers. Alternatively, the barrier flaps may be constructed using a spunbond fabric layer having a basis weight of about 0.4–1.0 oz/yd$^2$ (about 13–33 g/m$^2$). The spunbond fabric layer may consist of fibers made from polypropylene or a polypropylene/polyethylene copolymer composition.

Where a thermally bonded fabric is used as the fabric layer, it is desirable to minimize the amount of bonded area on the fabric to improve tactile and visual softness characteristics of the gusset-flap member. Preferably, the bonded area of the fabric is less than 25%. More preferably, the bonded area of the fabric is less than 15%. The percent bonded area can be measured by an analysis of an imprint of the bonding pattern produced by the bonding/embossing pattern die.

In the various configurations of the invention where selected materials or components, such as the barrier flaps provided by containment flap sections 144 and/or waist pocket sections 84, are configured to be permeable to gas while having a resistance and limited permeability to aqueous liquid, the liquid resistant material or component can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. Such "flexible" materials are compliant and will readily conform to the general shape and contours of the wearer's body. The backsheet 30 can help prevent the exudates contained in absorbent structure 32 from wetting articles such as bedsheets and overgarments which contact diaper 10.

In particular embodiments of the invention, backsheet 30 is a polyethylene film having a thickness of from about 0.012 millimeters (0.5 mil) to about 0.051 millimeters (2.0 mil). In the shown embodiment, for example, the backsheet is a film having a thickness of about 0.032 mm (about 1.25 mil). Alternative constructions of the backsheet may comprise a woven or non-woven fibrous web layer which has been totally or partially constructed or treated to impart a desired level of liquid impermeability to selected regions of the backsheet that are adjacent or proximate the absorbent body. For example, a clothlike backsheet may be composed of an approximately 0.5 oz/yd$^2$ (about 17 g/m$^2$) basis weight, polypropylene spunbond fabric which is laminated and thermally bonded to a stretch-thinned polypropylene film having a thickness of about 0.0006 inch (about 0.015 mm) and a film basis weight of about 14.5 g/m$^2$. Backsheet 30 typically provides the outer cover of the article. Optionally, however, the article may comprise a separate outer cover member which is in addition to the backsheet.

Backsheet 30 may optionally include a micro-porous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise provided with a matte finish to exhibit a more aesthetically pleasing appearance.

The size of the backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 5.0 centimeters (about 0.5 to 2.0 inch), to provide side margins.

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in selected regions, such as in areas along the diaper periphery, by a suitable attachment mechanism (not shown), such as an adhesive, sonic bonds, thermal bonds or any other attachment mechanism known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30. It should be readily appreciated that the above-described attachment mechanisms may also be employed to interconnect and assemble together the various other component parts of the article described herein.

In the representatively shown embodiment of the invention, the topsheet layer 28 is disposed and secured in facing relation with the backsheet layer 30 to retain and hold the retention portion 48 and the surge management 46 between the backsheet layer and the topsheet layer. The marginal side regions of topsheet layer 28 are operably connected to corresponding marginal side regions of the backsheet layer 30. Each of the attached marginal side regions of the topsheet and backsheet layers is located laterally outboard of its corresponding, associated side edge region of the surge management portion 46. In particular configurations of the invention, the topsheet 28 can include attached marginal end regions, which are located longitudinally outboard of the end edge regions of the retention portion 48 and/or surge management portion 46. Similarly, the backsheet 30 can include attached marginal end regions, which can be located longitudinally outboard of the end edge regions of the retention portion and/or surge management portion.

The leg elastic members, such as those provided by the elasticized leg gusset sections 142, are disposed adjacent the periphery of diaper 10 along each of the longitudinal side edge regions 20. The leg elastic members can be connected to either or both of the topsheet and backsheet layers to provide elasticized side margins of the diaper article, and can be arranged to draw and hold diaper 10 against the legs of the wearer to provide elasticized leg bands or leg cuffs. Waist elastic members, such as those provided by the flange section 82 of the waist member 80, may also be disposed adjacent either or both of the end edges of diaper 10 to provide elasticized waistbands.

The elastic members at the legband and waistband sections of the article are secured to the article in an elastically contractible condition so that in a normal under strain configuration, the elastic members effectively contract against the article. The elastic members can be secured in an elastically contractible condition in a number of ways; for example, the elastic members may be stretched and secured while the appointed component of the article is in an uncontracted condition. Alternatively, the component may be contracted, for example, by pleating, and the elastic members secured and connected to the component while the elastic members are in their relaxed or unstretched condition. Still other means, such as heat-shrink elastic material, may be used to gather the appointed component sections of the article.

The elastic members, such as elastomeric members 110, 118, 138 and 68, may have any of a variety of configurations. For example, the width of the individual elastic members may be varied from about 0.08 millimeters (0.003 inches) to about 25 millimeters (1.0 inches) or more. The elastic members may comprise a single strand of elastic material, or may comprise several parallel or non-parallel strands of elastic material, and the elastic members may be applied in a rectilinear or curvilinear arrangement. Where multiple strands are employed, the individual strands may be constructed to provide substantially equal elastic forces, or may be constructed to provide different elastic forces. For example, the individual strands may be of different diameter or other size, or may be configured with different amounts of elongation to thereby provide a gradient or other variation of elastic tensions. Where the strands are non-parallel, two or more of the strands may intersect or otherwise interconnect within the elastic member. The elastic members may be affixed to the appointed diaper components in any of several ways which are known in the art. For example, the elastic members may be ultrasonically bonded, heat and pressure sealed using a variety of bonding patterns, or adhesively bonded to diaper 10 with selected patterns of hotmelt or other type of adhesive. For example, sprayed or swirled adhesive patterns may be employed.

In particular embodiments of the invention, for example, each elastic strand is typically within the range of about 77–1050 decitex (dtx). In addition, elastics may be generally straight or optionally curved. For example, the curved elastics can be inwardly bowed toward the longitudinal centerline of the diaper. In particular arrangements, the curvature of the elastics may or may not be configured or positioned symmetrically relative to the lateral centerline of the diaper. The curved elastics may have an inwardly bowed and outwardly bowed, reflex-type of curvature, and the length-wise center of the elastics may be offset by a selected distance toward either the front or rear waistband of the diaper to provide desired fit and appearance.

Conventional articles have incorporated various barrier flap structures, such as the containment flaps 144 and the waist pocket sections 84, at their waistband and/or legband regions. For example, such articles have typically incorporated a single or multilayer piece of material, such as polymer films and film-nonwoven laminates, at the waistband portion of the article along the lateral cross-direction to form a waist flap or dam. The materials, however, typically exhibit similar behavior. When the materials are stretched, they have a tendency to neck down, thereby reducing their effective widths. As they neck down, they tend to form relatively large corrugations or furrows which extend substantially along the direction of stretching. The presence of such corrugations can cause the barrier flaps, particularly the waist flaps, to collapse upon themselves, thereby reducing the ability to remain open to receive and trap bodily waste materials. Additionally, when the conventional materials contract, they tend to decrease in overall stiffness, and this decrease in composite stiffness can again allow the barrier flaps to fold over or collapse upon themselves, thereby reducing their effectiveness.

It has been discovered that particular barrier flap structures, such as laminates incorporating individual and separated elastic strands, can provide structures which can overcome the shortcomings of prior structures. When stretched, the stranded laminates of the invention substantially avoid the undesired stretch-wise corrugating effect typically seen across the plane of the barrier flap and along the intended direction of stretch. Desirably, the amount of stretching does not exceed the amount of elongation at which the elastic strands were assembled into the laminate. When fully stretched and elongated, the stranded laminate can lay substantially flat. As the stranded laminate relaxes and elastically contracts, fine corrugations of sufficient size and frequency can be provided with the furrows or valleys of the corrugate generally aligned to extend substantially perpendicular to the direction of the contraction. The fine corrugations can enhance the stiffness of the flap structure and can improve its ability to remain open to receive waste materials. The stranded laminates of the present invention substantially avoid necking when stretched. Additionally, the geometry of the stranded laminates themselves play an important role in the performance of the materials when employed as a barrier dam structure, such as the shown waist dam and/or containment flap structures. The placement of the strands can also play a role in the functionality of the various configurations of the laminas.

It has been found, however, that the identifications of conventional types of materials or families of materials have not been adequate for deriving barrier flap structures that are sufficiently effective and reliable. It has been discovered that the performance and effectiveness of the barrier flap structure is dependent upon particular combinations of properties and behavior characteristics of the materials employed to assemble and construct the composite barrier flaps. For example, the incorporation of a flap composed of a polyurethane film or film laminate at the article waistband, and the placement of a flap composed of a SMS (spunbond-meltblown-spunbond) nonwoven fabric laminate at the article waistband have not reliably provided a sufficiently effective barrier flap structure. It is important to further configure the materials with particular physical properties, and one of the desired physical properties is the stiffness of the flap member.

The desired stiffness of the barrier flap member can be achieved in a variety of ways. For example, contributing factors include the basis weight of the flap materials, the stiffness or modulus of the individual components, the presence of adhesive or other bonding materials added to laminas within the flap member, the pattern and distribution of the applied adhesive or bonds, the presence of welding or ultrasonic treatments, the number and the elongation of the individual elastic strands employed in the barrier flap structure, the geometry of the strand placement within barrier flap, the presence and alignment of corrugations within the barrier flap, and the number of layers of components incorporated within the barrier flap.

Particular aspects of the invention can include distinctive combinations of component sizes and component stiffnesses. For example, the containment flap stiffness can have a Gurley stiffness value, as measured in a sample taken along the lateral cross-direction 24 of the article, which is at least about 10 milligrams-force (mgf). In other aspects, the cross-directional Gurley stiffness in the containment flap section can be not more than about 250 mgf, and optionally, can be not more than about 60 mgf to provide improved benefits. In addition, the leg gusset section can have a Gurley stiffness value, as measured in a sample taken along the lateral cross-direction 24 of the article, which is at least about 11 milligrams-force (mgf), and desirably is at least about 30 mgf. In further aspects, the cross-directional Gurley stiffness in the leg gusset section can be not more than about 250 mgf, and optionally, can be not more than about 120 mgf to provide improved benefits. In the various configurations of the invention, the Gurley stiffness of the leg gusset section (as measured with respect to a sample taken along the lateral cross-direction of the absorbent article) is substantially equal to or greater than the cross-directional Gurley stiffness of the containment flap section of the gusset-flap component.

With reference again to FIGS. 1, 2 and 3, the shown diaper article 10 may optionally have an elasticized waistband provided by a waist pocket member 80 which can include a laterally and longitudinally extending flange section 82, and a laterally and longitudinally extending barrier flap or pocket section 84. The flange section can, for example, be connected to the bodyside surface of the topsheet 28. The flap or pocket section 84 of the waist pocket member 80 includes a substantially fixed edge portion 102 which is secured to the article along and immediately adjacent the boundary of the flange section 82, and includes an elasticized, gathered moveable edge portion 104, which is longitudinally spaced from the fixed edge portion 102 by a selected distance. The pocket section thereby provides an operable waist dam and waist flap construction. The pocket section also includes a substantially liquid impermeable pocket barrier layer 106, and a pocket fabric layer 108 which is connected in facing relation with the pocket barrier layer. The pocket fabric may, for example be composed of a woven or nonwoven fabric, and in the shown arrangement, the fabric layer is desirably a nonwoven. A plurality of separate, laterally extending pocket elastic members 110 are sandwiched and operably connected between the pocket barrier layer 106 and the pocket fabric layer 108 to provide an elasticized waist pocket composite 112, which is gathered substantially along the lateral cross-direction 24 and is elastically stretchable at least along the cross-direction. Similarly, elastic members 118 can be arranged within the composite 112 to operatively elasticize the flange section 82. The shown arrangement includes elastics members which are aligned substantially parallel to one another, but optionally can include other separated configurations and alignments of the elastics. Desirably, the fabric layer 108 is arranged for placement against the wearer's skin, although the barrier layer 106 may optionally be appointed for placement immediately adjacent the wearer's skin. Suitable configurations for the waist pocket member 80 are described in U.S. patent application Ser. No. 560,525 which was filed Dec. 18, 1995 by D. R. Laux and entitled AN ABSORBENT ARTICLE WITH IMPROVED ELASTIC MARGINS AND CONTAINMENT SYSTEM (attorney docket No. 11,091); the entire disclosure of which is incorporated herein by reference in a manner that is consistent with the present disclosure.

The gusset-flap barrier layer 174 can be composed of a variety of materials, such as polymer films, fabrics or combinations thereof, having a relatively low permeability to aqueous liquid. The polymer films may, for example, be composed of polyolefins, polyesters, polyamides and the like, as well as combinations thereof. The fabrics may be woven or nonwoven, and the nonwoven materials can include spunbond-meltblown-spunbond (SMS) fabrics, meltblown fabrics, calendered nonwoven sheets and the like, as well as combinations thereof. With respect to the passage of liquid through its thickness, the barrier layer is constructed to exhibit a hydrohead of resistance which is sufficient to provide an operably effective barrier against the passage of liquids, such as urine.

The gusset-flap barrier layer 174 may, for example, be composed of a cast, embossed film having a thickness of about 0.015 mm (about 0.0006 inch), such as a CT XEM400.1 film; or a blown film having a thickness of about 0.010 mm (about 0.0004 inch), such as an XSF-367 film. Suitable films are available from Consolidated Thermoplastics, a business having offices in Chippewa Falls, Wis. The barrier layer may also be composed of a stretch-thinned film having a thickness of about 0.0089 mm (about 0.00035 inch), such as an XP1024A film available from Edison Plastics, a business having offices in Macalester, Okla. Alternatively, the barrier layer may be constructed with a breathable film having a thickness of about 0.0050 mm (about 0.0002 inch), such as a BF-303 film available from Exxon Plastics, a company having offices in Houston, Tex.

The gusset-flap fabric layer 176 is desirably a substantially continuously extending layer, and the gusset region 136 of the fabric layer is desirably contiguous with the containment flap region 63. In addition, the fabric layer 176 can be a substantially unsegmented, unitary layer. The gusset-flap fabric can be composed of a variety of materials, such as a fine denier, low basis weight, nonwoven fabric material. Examples of suitable nonwoven fabrics include polypropylene spunbond materials, bicomponent polypropylene-polyethylene spunbond materials, meltblown materials, SMS materials, through-air-bonded carded webs, point-bonded bonded-carded webs and the like, as well as combinations thereof. In particular arrangements, the fabric may be composed of a spunbond polypropylene which includes about 0–8% polyethylene copolymer, and desirably includes about 3% polyethylene copolymer.

In desired arrangements, the gusset-flap fabric layer 176 can have a basis weight of not less than about 3.4 g/m$^2$ (about 0.1 oz/yd$^2$). Alternatively, the basis weight can be not less than about 10.2 g/m$^2$ (about 0.3 oz/yd$^2$), and optionally can be not less than about 13.6 g/m$^2$ (about 0.4 oz/yd$^2$). In other aspects, the fabric layer 136 can have a basis weight of not more than about 272 g/m$^2$ (about 8 oz/yd$^2$). Alternatively, the basis weight can be not more than about 136 g/m$^2$ (about 4 oz/yd$^2$), and optionally can be not more than about 34 g/m$^2$ (about 1 oz/yd$^2$).

For example, the gusset-flap fabric layer can be a nonwoven fabric composed of polypropylene fibers wherein the fiber denier is not more than about 5 denier, and the fabric basis weight is about 17 g/m$^2$ (about 0.5 oz/yd$^2$). Alternatively, the fiber denier in the fabric layer can be not more than about 3 denier, and optionally can be not more than about 2.5 denier.

Desired arrangements of the article of the invention can be configured with each gusset-flap 19 connected directly or indirectly to an appointed section of an inwardly facing, bodyside surface of the topsheet layer 28. Optionally, the gusset-flap can be connected directly or indirectly to an appointed surface region of the backsheet layer 30. In the embodiment illustrated in FIG. 1, the elasticized gusset-flaps 19 extend along substantially the complete length of the intermediate region 16 of diaper 10. Alternatively, the gusset-flap members may extend the entire length of diaper 10, or any other length suitable providing the arrangement of elastically contractible lines desired for the particular diaper design.

In particular, each gusset-flap is connected along its associated, outwardly concave, terminal side edge contour 15 of the backsheet layer. Each of the side edge contours can have a longitudinal length 54 which desirably extends completely through the crotch region 18, and which may extend along at least about 20 percent of a total longitudinal length 180 of the article. In further configurations, the longitudinal length 54 of the side contour can be at least about 30 percent, alternatively can be at least about 40 percent, and optionally can be up to 100 percent of the total longitudinal length 180 of the article.

The leg elastics of the shown diaper 10 can be provided by the distinctive leg gusset sections 142 of the gusset-flaps 19. Each leg gusset section 142 can have a length thereof which extends along at least about 20 percent of the total longitudinal length 180 of the article. In other configurations, each leg gusset section 142 can extend along at least about 30 percent, and alternatively at least about 40 percent of the longitudinal length 180 of the article to provide improved effectiveness. If desired, each leg gusset section can extend along a length which can be up to 100 percent of the total longitudinal length of the article to provide further gasketing and containment. Alternatively, each leg gusset section can extend along a length which is not more than about 80 percent, and optionally is not more than about 70 percent of the total longitudinal length of the article to provide desired performance.

Additionally, each leg gusset section 142 can be in a bridging configuration across its associated, concave side edge contour 15 of the backsheet layer along a length 182 which is at least about 20 percent of the longitudinal length 180 of the article. In other configurations, each leg gusset section 142 can be in a bridging configuration across its associated, concave side edge contour 15 of the backsheet layer along a length 182 which is at least about 30 percent, and alternatively is at least about 40 percent of the extent of the longitudinal length 180 of the article to provide improved effectiveness. If desired, each leg gusset section can be in a bridging configuration along a length which can be up to 100 percent of the total longitudinal length of the article to provide further gasketing and containment. Alternatively, each leg gusset section can be in a bridging configuration along a length which is not more than about 80 percent, and optionally is not more than about 70 percent of the total longitudinal length of the article to provide desired performance and cost effectiveness.

In particular aspects of the invention, the gusset-flaps 19 are configured to substantially avoid intersecting the locations of the waist pocket members 80. Accordingly, the gusset-flaps can be constructed to terminate at positions which are spaced away from the terminal edges of the pocket sections 84 of the waist pocket members.

Figure 4:
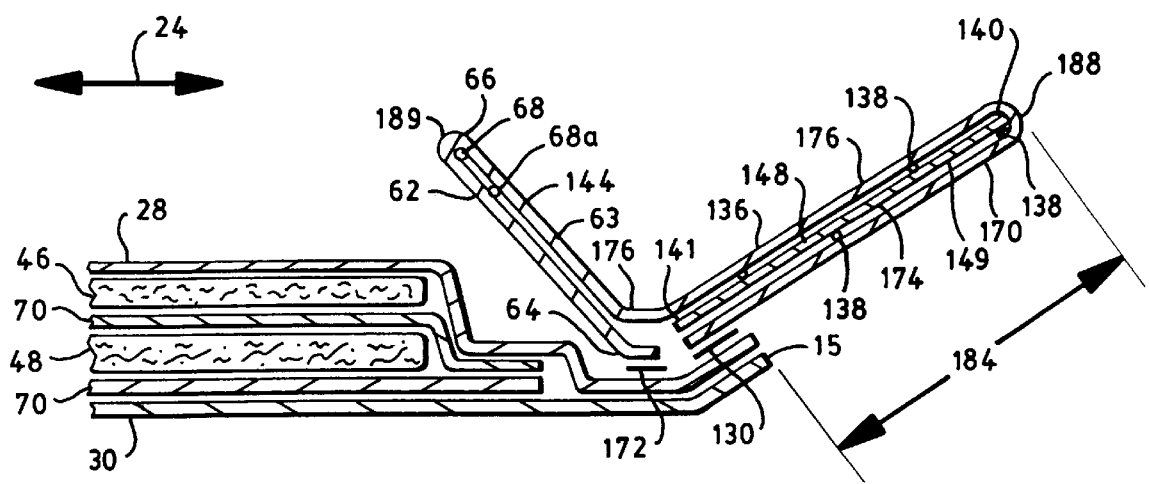
FIG. 4 a schematic, expanded, lateral cross-sectional view of one of the gusset-flap members taken through the crotch section of the article.
Figure 5:
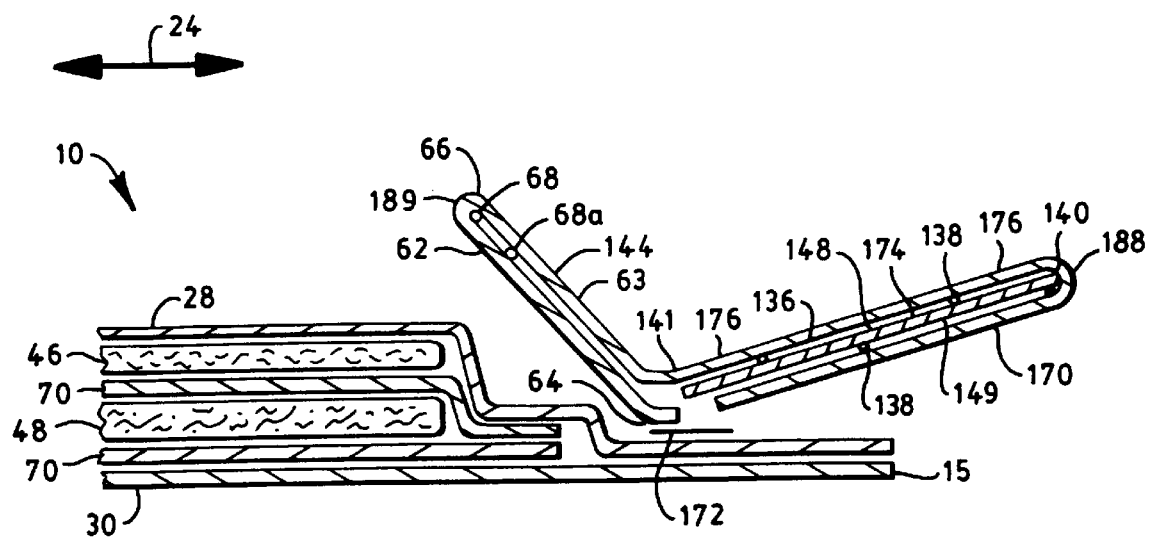
FIG. 5 a schematic, expanded, lateral cross-sectional view of one of the gusset-flap members and its adjacent containment flap section, taken through another section of the article.
Figure 6:
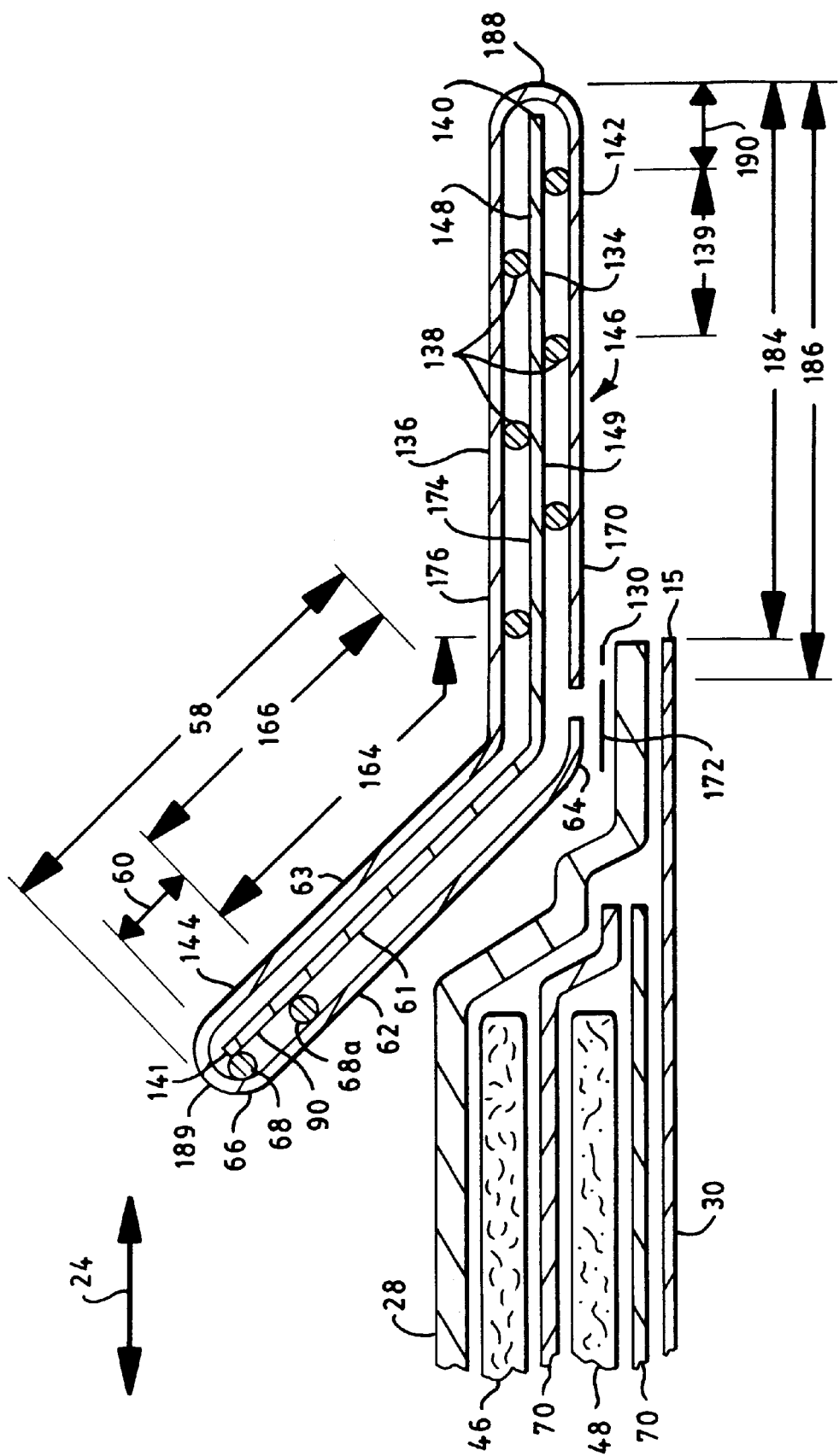
FIG. 6 a schematic, expanded, lateral cross-sectional view of a configuration of the gusset-flap member where the gusset flap barrier layer extends into the containment flap section.

With reference to FIGS. 1, 4 and 6, each of the side margins of the backsheet layer 30 generally defines a plane thereof, and each of the leg gusset sections 19 is constructed to extend past and beyond its associated concave side edge contour 15 of the backsheet layer 30 by a selected skirting distance 184, and in an arrangement which lies substantially within and substantially parallel to the plane of its associated backsheet side margin.

In the various arrangements of the invention, each leg gusset section 142 can include a leg gusset region 134 of the barrier layer 174, a leg gusset region 136 of the fabric layer 176 and a first arrangement of a first plurality of separate, longitudinally extending elastomeric members 138 sandwiched between the leg gusset region of the barrier layer and the cooperating, corresponding portions of the leg gusset regions of the fabric layer to provide an elastomeric composite which is substantially longitudinally gathered. In particular arrangements, the barrier layer region 134 and the fabric layer region 136 can be substantially coextensive. The elastomeric members can be arranged in any desired alignment or configuration, such as parallel, non-parallel, straight, curvilinear or combinations thereof. Alternatively, the complete leg gusset portion of the gusset-flap, or the containment flap portion of the gusset-flap, or the entire gusset-flap may also be placed in the absorbent article in a parallel, non-parallel, straight, curvilinear, or any combination thereof. Desirably, the fabric layer region 136, particularly the folded over, outboard side portion 170, is arranged for placement against the wearer's skin. Optionally, the barrier layer region 134 may be appointed for placement immediately adjacent the wearer's skin.

In particular aspects, the illustrated barrier layer region 134 is substantially coextensive with its corresponding leg gusset section 142 at least in the portion of the leg gusset section which bridges and spans across the C-shaped gap formed by terminal edge of the corresponding side contour of the backsheet 30. The barrier layer 174 may or may not extend into the adjacent containment flap section 144 of the gusset-flap member, as desired.

With reference to the representative arrangements shown in FIGS. 4 and 6, the leg gusset region 136 of the fabric layer 176 can be positioned and joined immediately adjacent to the first, relatively inward surface 148 of the barrier layer 174. The outboard side portion 170 of the fabric layer extends beyond the first, relatively outboard side edge 140 of the barrier layer 174, and the fabric layer has an appointed, first folding line or region 188 which is positioned generally adjacent to the side edge 140 of the barrier layer. The fabric layer side portion 170 is operatively folded and wrapped around the barrier layer side edge 140 to thereby enclose the resultant wrapped edge of the barrier layer. The fabric layer side portion 170 then extends along the second major surface 149 of the barrier layer 174 in a direction toward the center of the article. Desirably, the fabric side portion 170 overlies a substantial entirety of the second major surface 149 of the barrier layer region 134 in the leg gusset section 142, and substantially completely covers the second major surface of the portion of the barrier layer which is located in the leg gusset section 142. Accordingly, the fabric side portion 170 can be interposed between the barrier layer and the wearer's skin.

The folding line 188 is spaced from the first edge 140 of the barrier layer by a distance 190 (FIG. 6) of not more than about 8 mm. Alternatively, the folding line 188 is spaced from the first edge 140 of the barrier layer by a distance which is not more than about 4 mm and optionally is not more than about 2 mm to provide improved performance. Desirably, the spacing distance 190 is substantially zero. If the spacing distance 190 is too large, there may be excessive wicking or leakage of liquids around the edge of the barrier layer.

Figure 9:
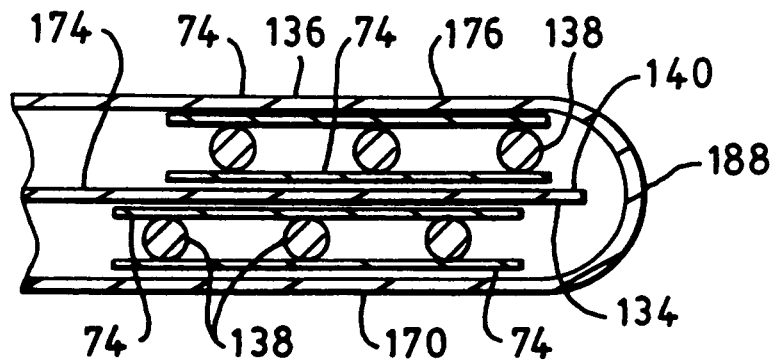
FIG. 9 a schematic of a portion of an expanded, lateral cross-sectional view showing distributions of adhesive which bond the elastomeric strands into the leg gusset portion the gusset-flap member.

Each of the elastic members 138 of the leg gusset section 142 are sandwiched between the barrier layer 174 and at least a portion of the fabric layer 176 in the leg gusset section of the gusset-flap 19. Each elastic member is attached to at least one of the barrier and fabric layers with a selected pattern of bonding, such as a pattern of adhesive. In particular arrangements, the elastic members 138 can be attached with one or more individual strips of adhesive 74, as representatively shown in FIGS. 9 and 10. Each adhesive strip 74 is configured to attach one or more of the elastomeric members 138 to at least one of the barrier and fabric layers.

Figure 10:
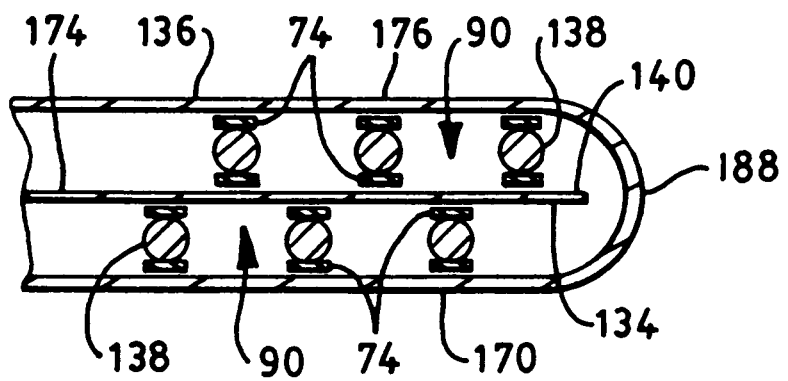
FIG. 10 a schematic of a portion of an expanded, lateral cross-sectional view of a distribution of individual adhesive strips which attach the elastomeric strands into the leg gusset portion the gusset-flap member.

In a particular aspect of the invention, each individual adhesive strip can be spatially separated from laterally adjacent adhesive strips by a discrete distance, as representatively shown in FIG. 10. With the illustrated arrangement, each adhesive strip 74 is configured to attach substantially a one of the elastomeric members 138 to at least one of the barrier and fabric layers, and the barrier layer 174 and the fabric layer 176 in the leg gusset section 142 are substantially unattached to each other at intermediate regions 90 located between immediately adjacent members of the first plurality of elastomeric members 138. Thus, each elastic member of the first plurality of elastomeric members 138 in each of the leg gusset sections 142 can be attached to at least one of the barrier layer 174 and/or fabric layer 176 with a substantially separately provided strip of adhesive 74. The individual, spatially separated adhesive strips substantially avoid touching one another. As a result, the substantially unattached intermediate regions 90 can blouse and more effectively form a cushioning topography.

Figure 11:
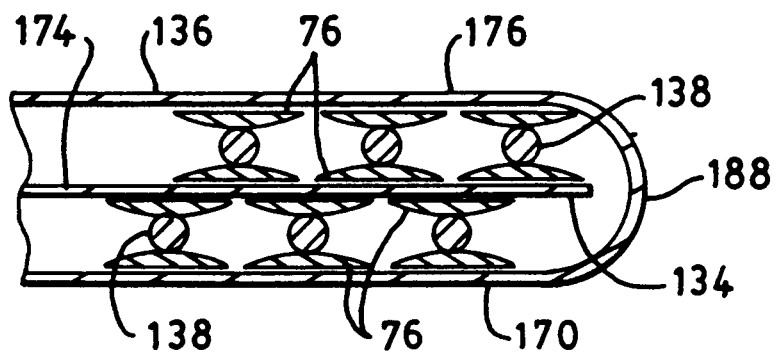
FIG. 11 a schematic of a portion of an expanded, lateral cross-sectional view of another pattern distribution of adhesive add-ons which attach the elastomeric strands in the leg gusset portion of the gusset-flap member.

In other arrangements of the invention representatively shown in FIG. 11, an adhesive pattern distribution 76 can be configured to concentrate the placement of adhesive at the locations of the elastic members 138, while delivering significantly reduced amounts of adhesive is in the areas between the elastic members 138, in the boundary space 164 between the containment flap elastics and the leg gusset elastics, and/or in the folding line area 188. In additional aspects, the barrier layer 174 and the fabric layer 176 in the leg gusset section 142 can be attached to each other with a lesser, reduced adhesive amount at one or more of the intermediate areas which are interposed between immediately adjacent members of the first plurality of elastomeric members 138, as compared to the adhesive amount located at the positions of the first plurality of elastomeric members to secure and laminate the first plurality of elastomeric members. Similarly, where the barrier layer extends into the containment flap section 144, the barrier layer 174 and the fabric layer 176 in the containment flap section 144 can be attached to each other with a reduced adhesive amount at one or more of the intermediate areas which are interposed between immediately adjacent members of the second plurality of elastomeric members 68, as compared to the adhesive amount located at the positions of the second plurality of elastomeric members to secure and laminate the second plurality of elastomeric members.

With regard to the containment flap section 144, the second arrangement of at least one elastomeric member can be attached to at least one of the gusset-flap barrier and fabric layers 174, 176 with an increased amount of adhesive, as compared to the amount of adhesive located in the boundary space 164 between the first arrangement of leg-gusset elastics 138 and the second arrangement of containment flap elastics 68. Where the containment flap section 144 includes a second arrangement having a second plurality of elastomeric members, the elastomeric members can be attached to at least one of the gusset-flap barrier and fabric layers 174, 176 (particularly the fabric layer) with an increased, greater amount of adhesive, as compared to the amount of adhesive located at intermediate regions which positioned between immediately adjacent members of the second plurality of containment flap elastics. Where the barrier layer 174 extends into the containment flap section 144 and the second arrangement of containment flap elastics includes a second plurality of elastomeric members 68, the second plurality of elastomeric members can be laminated to the gusset-flap barrier and fabric layers with a greater amount of adhesive, as compared to the adhesive amount located at intermediate regions which positioned between immediately adjacent members of the second plurality of containment flap elastics.

While such arrangements may or may not have a discrete spacing between the area array of applied adhesive 76, it has been noted that this arrangement can provide sufficient adhesive bonding without unduly stiffening the leg gusset portion of the gusset-flap composite. This arrangement can also form a more cushioning topography in the leg gusset portion of gusset-flap.

Suitable techniques for applying a desired pattern of adhesive are described in U.S. Pat. No. 5,340,648 entitled ELONGATED ELEMENT COMPRISING HELICALLY PATTERNED ADHESIVE granted Aug. 23, 1994 to N. Rollins et al; U.S. Pat. No. 5,501,756 granted Mar. 26, 1996 to N. Rollins et al.; and U.S. Pat. No. 5,507,909 granted Apr. 16, 1996 to N. Rollins et al. The entire disclosures of these documents are incorporated herein by reference in a manner that is consistent herewith.

Figure 7:
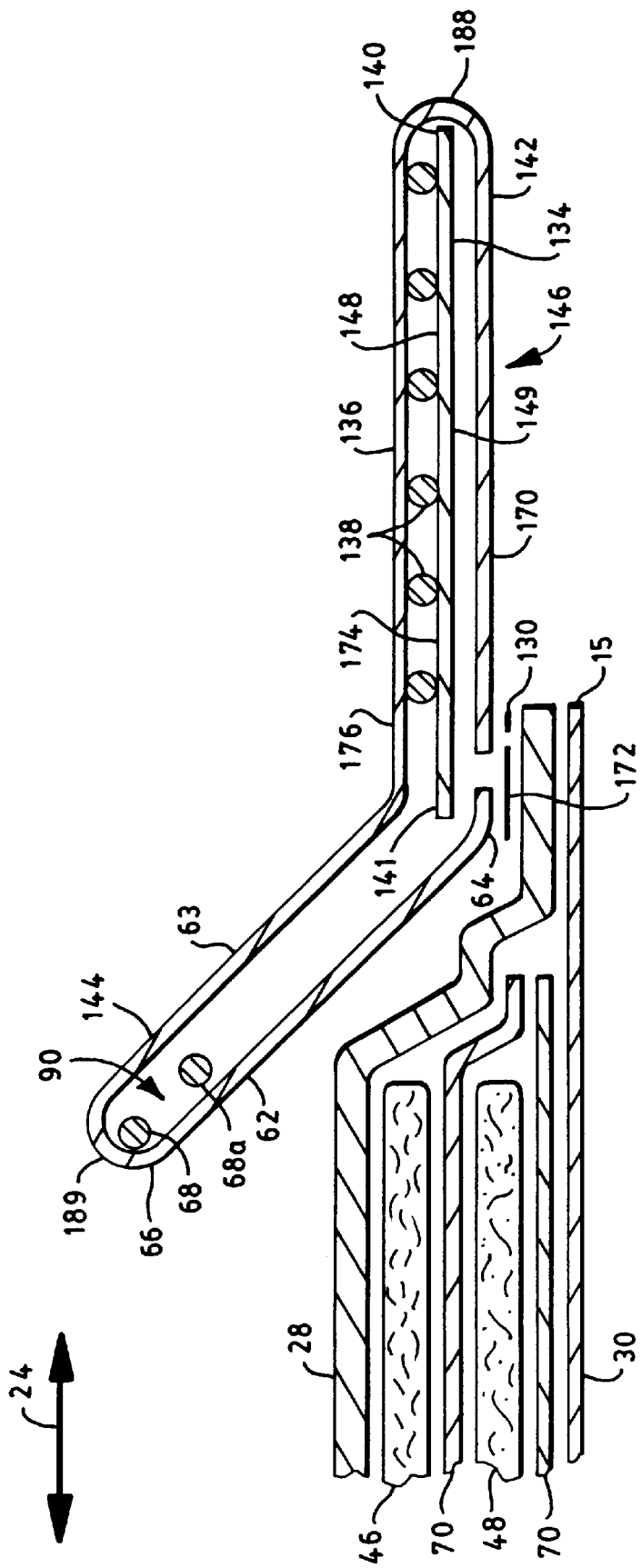
FIG. 7 a schematic, expanded, lateral cross-sectional view of an alternative configuration of one of the gusset-flap members taken through the crotch section of the article.
Figure 8:
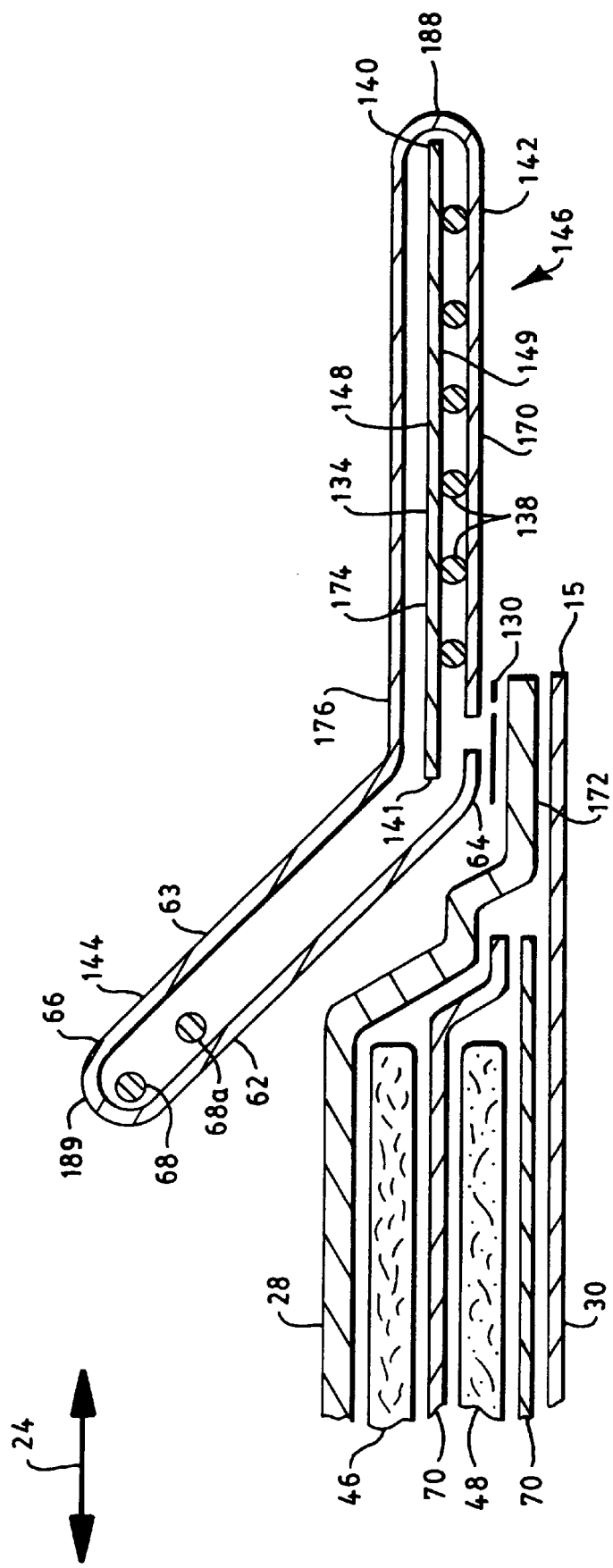
FIG. 8 a schematic, expanded, lateral cross-sectional view of still another arrangement of the gusset-flap member.

All of the elastomeric members 138 can be attached on one single surface of the leg gusset region 134 of the barrier layer 174. For example, all of the elestomeric members 138 can be attached on the first major surface 148 and covered by the primary, base portion of the leg gusset region 134 of the fabric layer 176 (FIG. 7). Alternatively, all of the elastomeric members 138 can be attached on the second major surface 149 and covered by the outboard side portion 170 of the fabric layer (FIG. 8).

In another aspect, each of the leg gusset sections 142 can be configured with the first arrangement of elastomeric members 138 including a first sub-set of laterally spaced-apart elastomeric members joined to the first major surface 148 of the barrier layer 174, and a second sub-set of laterally spaced-apart elastomeric members joined to the second major surface 149 of the barrier layer (FIGS. 4 and 6). In desired arrangements, the first sub-set of elastomeric members can be laterally offset and staggered with respect to the second sub-set of elastomeric members. More particularly, the first subset of elastomeric members can be arranged with a first set of gaps between adjacent members, and the second sub-set of elastomeric members can be arranged with a second set of gaps between adjacent members. When observing across the thickness dimension of the barrier layer 174, the first sub-set of elastomeric members are substantially aligned with the second set of gaps, and the second sub-set of elastomeric members are substantially aligned with the first set of gaps.

In yet another aspect of the invention, adjacent elastomeric members 138 can have a spacing distance 139 (FIG. 6) therebetween which is not less than about 1 mm. Alternatively, the spacing distance can be not less than about 3 mm, and optionally can be not less than about 4 mm. In further aspects of the invention, the adjacent elastomeric members 138 can have a spacing distance 139 therebetween which is not more than about 45 mm. Alternatively, the spacing distance can be not more than about 35 mm, and optionally can be not more than about 25 mm.

The elastomeric members 138 within each leg gusset section 142 can be configured to provide for a composite elastic tension which is not less than about 50 grams-force when the leg gusset section composite is stretched to a length which is 90 percent of its substantially flat-out, uncontracted, extended length. The composite elastic tension can alternatively be not less than about 75 grams-force and optionally can be not less than about 100 grams-force to provide an improved combination of comfort and containment. In other aspects of the invention, the elastomeric members 138 within each leg gusset section 142 can be configured to provide for a composite elastic tension which is not more than about 300 grams-force when the leg gusset section composite is stretched to 90 percent of its flat-out, uncontracted length. The composite elastic tension can alternatively be not more than about 250 grams-force and optionally can be not more than about 200 grams-force to provide desired combinations of comfort and containment.

In the various configurations of the invention, each leg gusset section 142 can have a lateral width 186 (FIG. 6) which is not less than a minimum of about 13 mm. The lateral width of the leg gusset section can alternatively be not less than about 19 mm, and optionally can be not less than 25 mm. In further aspects of the invention, each leg gusset section 142 can have a lateral width 186 which is not more than about 104 mm. The lateral width of the leg gusset section can alternatively be not more than about 76 mm, and optionally can be not more than about 51 mm. Additionally, particular aspects of the invention can be configured with each leg gusset section having a gusset width 186 which is greater than a lateral width of its corresponding containment flap section 144.

In desired configurations, each leg gusset section 142 can extend laterally beyond its associated side edge contour 15 of the backsheet layer 30 by a skirting distance 184 of not less than about 3 mm. Alternatively, the skirting distance can be not less than about 6 mm and optionally can be not less than about 9 mm, at least within the crotch section 18 of the article. In other aspects of the invention, each leg gusset section 142 can extend laterally beyond its associated side edge contour 15 of the backsheet layer 30 by a skirting distance of not more than about 60 mm. Alternatively, the skirting distance 184 can be not more than about 45 mm, and optionally can be not more than about 35 mm, at least within the crotch section 18 of the article, to provide improved comfort and gasketing. It is also desirable to configure the skirting distance to provide a substantially complete coverage of the buttocks of the wearer.

The various configurations of the leg gusset section 142 can provide a plurality of separate, longitudinally extending elastomeric members which are laterally spaced outboard from the longitudinally extending, terminal side edge of the backsheet layer by a discrete distance, at least within the crotch region of the article. Such laterally spaced elastomeric members can substantially avoid having a direct connection to said backsheet layer and can substantially avoid providing a direct gathering of said backsheet layer in its crotch region.

As representatively shown in FIGS. 4 and 6, each leg gusset section 142 is connected to the article, particularly with the bodyside surface of topsheet 28, with a leg gusset attachment 172, which holds the gusset section 142 substantially parallel to a plane generally defined by its associated side margin of the backsheet 30. More particularly, the gusset attachment 172 includes an article attachment which secures the leg gusset section 142 to the article adjacent to its associated outwardly concave terminal side edge contour 15 of the backsheet layer 30 along substantially an entire length of the side edge contour within which the leg gusset 142 and its correspondingly associated side edge contour 15 are coextensive. In particular aspects of the invention, the securement of each gusset section to the article substantially ends at a location which is laterally outboard of the absorbent body structure 32, at least within the crotch portion 18 of the article. Accordingly, the securement of the leg gusset section to the crotch portion article substantially ends at a location which is laterally outboard of the retention portion 48. Additionally, the securement of the gusset section 142 to the crotch portion of the article can substantially end at a location which is laterally outboard of the wrapsheet 70. In the shown arrangements, for example, the leg gusset attachment 172 can have a generally U-shape configuration, with the bottom of the U-shape extending generally longitudinally and the two arms of the U-shape extending generally laterally. The shown U-shape is angular, but may be nonangular, if desired.

With reference to FIGS. 1 and 4, further aspects of the invention can include a gusset perimeter bond 130 which attaches a terminal side edge of the topsheet 28 and/or backsheet 30 to the leg gusset section 142 at least within the crotch region of the article. The perimeter bond 130 may extend through the complete longitudinal length of the diaper 10. The perimeter bond 130 may optionally be configured to not extend over the complete length of the overlap of the gusset section 142 with the terminal, side edge margins of the topsheet and backsheet layers which corresponds to each of the gusset sections 142. In particular aspects, the gusset perimeter bond 130 has a longitudinal extent 132 of not more than about 90% of the total, overall length 180 of the article. The longitudinal extent 132 of the gusset perimeter bond can alternatively be not more than about 80%, and optionally can be not more than about 60% of the length of the article. As a result, a portion of either or both of the longitudinal end portions 150 of each gusset section 142 can move substantially independently its immediately adjacent portions of side margin of the topsheet and backsheet layers, while also causing the side margins of the topsheet and backsheet layers within the crotch section of article to move in a substantial correspondence and compliance with the portion of the gusset section 142 located in the crotch section.

The gusset perimeter bond 130 can be a substantially continuous bond, or may alternatively be a discontinuous bond composed of a regular or irregular pattern of attachments. In the illustrated configuration, for example, the gusset perimeter bond can be provided by a selected pattern of discrete sonic bonds which are distributed over a selected bonding area. The bonding area can have a lateral width which is at least about 0.2 cm, and alternatively is at least about 1 cm. In other aspects the lateral width of the bonding area can be up to about 8 cm, and optionally, can be up to about 15 cm to provide improved performance. The gusset perimeter bond can be substantially straight, or can be curved to substantially follow the terminal edges of the topsheet and/or backsheet layers. In addition, the laterally outboard edge of at least a portion of the perimeter bond 130, particularly within the crotch region of the article, can be substantially coterminous with the laterally terminal edges of the topsheet and/or backsheet layers to provide improved aesthetics and performance.

Each leg gusset section 142 includes a first arrangement of a first plurality of two or more separate, longitudinally extending elastomeric members 138 which are laterally spaced outboard from the side edge contour 15 of the backsheet layer 30 by a discrete distance, at least within the crotch region 18 of the article. In desired arrangements, the laterally spaced elastomeric members substantially avoid having a lamination onto or other direct or immediate connection to the backsheet layer 30 and thereby substantially avoid providing a direct gathering of the backsheet layer 30, at least within the crotch region 18 of the article.

In particular aspects of the invention, the leg gusset section 142 can have a composite stiffness which is not less than about 5 mg. The composite stiffness can alternatively be not less than about 10 mg, and optionally can be not less than about 15 mg. In other aspects of the invention, the leg gusset section 142 can have a composite stiffness which is not more than about 250 mg. The composite stiffness can alternatively be not more than about 200 mg, and optionally can be not more than about 170 mg.

The stiffnesses of the various components and sections of the article of the invention can be determined by employing the test methodology of TAPPI T543 om-94, and by employing a Gurley Digital Stiffness tester, Model 4171-D, a device available from Teledyne Gurley, a business having offices located in Troy, N.Y. Accordingly, the stiffness values of the various sections of the article, such as the waist pocket member 80, are bending stiffnesses. The stiffnesses can be expressed as milligrams (mg) which correspond to milligrams-force, or may be expressed in terms of the numerically equivalent values of Standard Gurley Units (SGU). For the purposes of the present invention, the axis about which a bending moment is applied to the sample during the stiffness testing is a bending axis which is aligned substantially parallel to the direction of elastic stretch and gathering provided by the associated elastic members, such as elastic members 138 and/or 68. For example, the stiffness of the leg gusset section 142 is taken with respect to the cross-dimension of the article. The stiffness is determined with respect to a bending moment which is applied about a bending axis that is generally aligned along the longitudinal dimension 26 of the article. A suitable device for taking the stiffness measurements is a Gurley Digital Stiffness tester, Model 4171-D, available from Teledyne Gurley, a business having offices in Troy, N.Y.; or an equivalent device. A suitable testing procedure is TAPPI T543 om-94.

The various configurations of the gusset-flaps 19 can advantageously include elasticized, barrier flaps, such as the illustrated containment flap sections 144 at the legband regions of the diaper. The shown configurations, for example, include two containment flap sections 144 which are operably connected to extend above and over the bodyside surface of the topsheet layer 28. Alternative, constructions and arrangements for the containment flap sections 144 are, for example, described in U.S. Pat. No. 4,704,116 issued Nov. 3, 1987, to K. Enloe, the disclosure of which is hereby incorporated by reference in a manner that is consistent (not contradictory) herewith. Other alternative configurations of the containment flap sections 144 are described in U.S. Pat. No. 5,562,650 entitled ABSORBENT ARTICLE HAVING AN IMPROVED SURGE MANAGEMENT which issued Oct. 8, 1996 to R. Everett et al. (attorney docket No. 11,375), the disclosure of which is hereby incorporated by reference in a manner that is consistent herewith.

The containment flap sections 144 can be attached to the topsheet layer 28 along length-wise extending fixed regions, such as fixed edges 64, of the flap sections. A movable edge 66 of each containment flap section includes a selected, second arrangement of flap elastic member 68 which can comprise one or more individual strands of elastomeric material. For example, a plurality of elastic strands may be configured in a spatially separated, generally parallel arrangement, and a suitable elastic strand can, for example, be composed of a 470 decitex LYCRA elastomer which is available from E.I. DuPont de Nemours, a business having offices in Wilmington, Del. Alternatively, the elastic strands may be composed of 700 denier GLOSPAN S7 spandex elastomer which is available from Globe Manufacturing, a business having offices in Fall River, Mass.

Each elastic member 68 is connected to the movable edge of the containment flap section 144 in an elastically contractible condition such that the contraction of the elastic components thereof gathers and shortens the edge of the containment flap section. As a result, the movable edge of each containment flap section tends to position itself in a spaced relation away from the bodyside surfaces of topsheet 28 and/or surge management portion 46 toward a generally upright and approximately perpendicular configuration, especially in the crotch section 18 of the diaper. In the shown embodiment, for example, the moveable edge of the containment flap section is operatively connected to the flap elastics by partially folding or otherwise doubling the flap material back upon itself by a limited amount which is sufficient to enclose the selected arrangement of the elastics 68 located in the flap section 144. More particularly, the inboard side portion 62 of the fabric layer can be folded or otherwise wrapped around an appointed second folding line 189. The elastomeric members 68 can then be sandwiched or otherwise contained between two laminations of the fabric 176. In addition, the inboard side portion 62 of fabric layer and the primary, base portion of the containment flap section 63 of the fabric layer can be substantially unattached to each other at intermediate regions 90 located between immediately adjacent members of the first plurality of elastomeric members 138. For example, each elastic member of the first plurality of elastomeric members 68 in each of the containment flap sections 144 can be attached to its corresponding portions of the fabric layer 176 with a substantially separate strip of adhesive. The individual, spatially separated adhesive strips substantially avoid touching one another. As a result, the substantially unattached intermediate regions 90 can blouse and more effectively form a cushioning topography.

In other arrangements of the invention, an adhesive spray can be configured to concentrate the adhesive spray at the positions of the elastic members 68 while depositing minimal amounts of adhesive is in the spaces 90 between the elastic members 68, in the space 164 separating the containment flap elastics 68 from the leg gusset elastics 138, and/or in the folding line area 189. While there may or may not be a discrete spacing between the areas of applied adhesive in this particular arrangement, it has been noted that this arrangement provides sufficient adhesive bonding without unduly stiffening the containment flap portion of the gusset-flap composite. This arrangement can also help form a more cushioning topography in the containment flap portion of the gusset-flap.

At least a pair of the containment, barrier flap sections 144 are connected and disposed along laterally opposed, longitudinally extending regions of topsheet layer 28, and the connected topsheet regions are located generally adjacent to laterally opposed side edge regions of the medial section of topsheet layer 28. The connected topsheet regions are located substantially laterally inboard of the leg gusset sections 142 of the diaper article 10, but portions of the connected regions of the topsheet may optionally be located outboard of the leg gusset sections.

Each containment flap section 144 includes at least one of the elastomeric members 68 attached to the containment flap section at a location which is proximate to the movable edge 66 of the containment flap section. In particular configurations, at least one of the elastomeric members 68 is attached to the containment flap section at a location which is proximate to the substantially fixed edge 64 of the containment flap section.

With reference to FIG. 6, each containment flap section 144 may include one or more elastomeric members with at least one base elastomeric member 68a which is attached to the containment flap section 144 at a location which is between the movable edge portion 66 and the substantially fixed edge 64 of the containment flap section. In particular configurations, the base elastomeric member 68a can be attached to the containment flap section 144 at a location which is proximate the movable edge portion 66 of the containment flap section. The base elastic member may have a spacing distance 166 with an upper bound which is not more than about 37 mm from the fixed edge 64 of the containment flap section, at least within the crotch portion 18 of the article. In particular arrangements, the at least one base elastomeric member can be attached substantially immediately adjacent to the fixed edge 64 of the containment flap section 144.

In particular aspects of the invention, adjacent elastomeric members 68 can have a spacing distance 60 which is not less than about 2 mm. The spacing distance between the adjacent elastomeric members 68 can alternatively be not less than about 2 mm, and optionally can be not less than about 4 mm. In other aspects, the adjacent elastomeric members 68 can have a spacing distance 60 which is not more than about 25 mm. The spacing distance between adjacent elastomeric members 68 can alternatively be not more than about 13 mm, and optionally can be not more than about 8 mm to provide desired effectiveness.

In desired arrangements, each containment flap section 144 can have a lateral width dimension 58 (FIG. 6) of at least about 13 mm, and in particular aspects of the invention, the containment flap width is less than the width 186 of its corresponding leg gusset section 142. Additionally, each containment flap section 144 may have a longitudinal length which is substantially equal to the overall, total length 180 (FIG. 1) of the article. Alternatively, each containment flap section may have a length which is less than the overall, total length of the article, and the shorter containment flap section may be configured with a zoned-placement at a selected location along an appointed portion of the overall length of the article. For example, the length of the containment flap section may be substantially centrally located along the article length, or may be positioned with an offset toward the front or back waistband of the article. Optionally, each containment flap section may have a length which is substantially equal to or less than the overall, total length of the absorbent body structure 32, and the relatively shorter containment flap section may be configured with a zoned-placement at a selected location along an appointed portion of the overall length of the absorbent body structure.

The containment flap sections 144 are operably secured to appointed sections of the article, such as laterally opposed sections of the topsheet layer 28, with a suitable attachment mechanism 172. In the shown arrangements, for example, the containment flap attachments can be similar to those employed with the waist pocket member 80. The attachments can have a generally U-shape configuration, with the bottom of the U-shape extending generally longitudinally and the two arms of the U-shape extending generally laterally. The shown U-shape is angular, but may be non-angular, if desired. As illustrated in the shown arrangements, the flap attachments can be operatively combined and integrated with the leg gusset attachments 172. Alternatively, the flap attachments can be distinct and separate from the leg gusset attachments, if desired.

With reference to FIG. 6, a further aspect of the invention can have an optional configuration wherein the barrier layer 174 is extended into the containment flap section 144 of each leg-gusset 19. As a result, the relatively inboard, second side edge 141 of the barrier layer 174 is located within the containment flap section 144. With this arrangement, the inboard portion 62 of the fabric layer 176 extends beyond and past the corresponding, longitudinally extending, second side edge 141 of the barrier layer. The fabric side portion 62 is appointed for folding and wrapping about its appointed, second folding line or region 189 to extend across and over at least the portion the second major surface 149 which is located in the containment flap section 144. Accordingly, the relative arrangements of the barrier layer region 61, the fabric layer region 63 and the second array of elastomeric members 68 within the containment flap sections 144 can be similar to the arrangements of the similar components provided in the leg gusset sections 142. For example, the fabric side portion 62 can overlie a substantial entirety of the second major surface 149 of the barrier layer region 61 in the flap section 144, and can substantially completely cover the second major surface of the portion of the barrier layer which is located in the containment flap section 144.

Accordingly, the fabric side portion 62 can be interposed between the barrier layer and the wearer's skin.

The arrangement or array of elastomeric members 68 in each containment flap section 144 can be attached to at least one of the barrier and fabric layer regions 61 and 63, respectively, with a suitable securing mechanism, such as a selected pattern of adhesive or other type of bonding. For example, the adhesive may be applied by spraying adhesive discontinuous droplets or filaments, and/or may be applied by arranging generally continuous lines of adhesive in a selected pattern, such as a swirl pattern. Alternatively, the hot melt spray pattern may be concentrated in the vicinity of the elastomeric strands, although a limited, reduced amount of adhesive may be in the interstitial spaces between the elastomeric strands. Alternatively, the elastomeric members 68 can be attached to at least one of the barrier and fabric layers with a plurality of individual, longitudinally extending strips of adhesive. Each individual adhesive strip is spatially separated from immediately adjacent adhesive strips by a discrete distance, and each individual adhesive strip is arranged to attach substantially an individual one of the elastomeric members 68 to the at least one of the barrier and fabric layers. In the shown arrangements, for example, the strips of adhesive can be aligned substantially parallel to one another.

In a particular aspect of the invention, the fabric layer 176 and the barrier layer in the containment flap section 144 are substantially unattached to each other at intermediate regions 90 (FIG. 6) located between immediately adjacent members of the second plurality of elastomeric members 68.

In another aspect of the invention, each elastic member of the second plurality of elastomeric members 68 of the containment flap sections 144 can be attached to at least one of the flap region 61 of the barrier layer and/or the containment flap regions of the fabric layer 176 with a substantially separate strip of adhesive in a manner similar to that employed in the construction of the leg gusset section 142. Accordingly, the individual, spatially separated adhesive strips substantially avoid touching one another, and the substantially unattached intermediate regions 90 can blouse and more effectively form a cushioning topography.

In another aspect of the invention, the fabric layer 176 and the barrier layer in the containment flap section 144 may be lightly attached with hot melt adhesive at the intermediate regions 90 located between immediately adjacent members of the second plurality of elastomeric members 68, but with the bulk of the hot melt adhesive concentrated at the locations of the elastomeric strands 68. In another aspect of the invention, each elastic member of the second plurality of elastomeric members 68 of the containment flap sections 144 can be attached to at least one of the flap regions 61 of the barrier layer and/or the containment flap regions of the fabric layer 176 with a heavier concentration of adhesive 74 at the elastomeric strands 68 in a manner similar to that employed in the construction of the leg gusset section 142. Accordingly, the lightly attached intermediate regions 90 can more readily blouse and more effectively form a cushioning topography.

All of the elastomeric members 68 can be attached on one single surface of the containment flap region 61 of the barrier layer. For example, all of the elastomeric members 68 can be attached on the first major surface 148 and covered by the primary, base portion of the containment flap region 63 of the fabric layer (FIG. 7). Alternatively, all of the elastomeric members 68 can be attached on the second major surface 149 and covered by the inboard side portion 62 of the fabric layer (FIG. 8).

The second arrangement elastomeric members 68 may also include a second a first sub-set of individual elastomeric members joined to the first major surface 148 of the barrier layer 174, and a second sub-set of individual elastomeric members joined to the second major surface 149 of the barrier layer (FIGS. 4 and 6). In addition, the first and second sub-sets of elastomeric members can be arranged in a laterally offset and staggered configuration.

In other arrangements of the invention, the elastic members 68 in the containment flap section 144 can be spaced from the closest elastic members 138 in the gusset section 142 by a predetermined boundary space 164 (FIG. 6) which provides a minimum separation distance of at least about 2 mm. In particular aspects, the separation distance provided by the boundary spacing distance is at least about 8 mm, and optionally is at least about 16 mm. The separation distance provides an amount of isolation which effectively permits the containment flap elastic members 68 to operate substantially separately from the gusset elastic members 138. Accordingly, the gathering provided by the containment flap elastics can be substantially separated from the gathering provided by the gusset elastics.

In particular aspects of the invention, each containment flap section 144 has a composite stiffness of at least about 5 mg, taken with respect to the cross dimension of the article.

For the purpose of the present invention, the stiffness of the containment flap section is determined with respect to a bending moment which is applied about a bending axis that is substantially aligned along the longitudinal dimension 26 of the article. Desirably, the containment flap section has a composite stiffness which is not less than about 10 mg, and alternatively, is not less than about 15 mg to provide improved containment. In further aspects, the containment flap section can have a composite stiffness which is not more than about 250 mg. The composite stiffness can alternatively be not more than about 200 mg, and optionally can be not more than about 170 mg to provide desired performance. If the stiffness of the containment flap section 144 is too low, the containment flap section may excessively collapse upon itself. If the stiffness of the containment flap section is too high, there may be excessive irritation of the wearer's skin.

As representatively shown, the article of the invention can be configured with each gusset-flap 19 connected directly or indirectly to an inwardly facing, appointed bodyside surface of the topsheet layer 28. Each gusset-flap member 19 can have a longitudinal length thereof which (as an approximate lower bound) extends along at least about 20 percent of the total longitudinal length 180 (FIG. 1) of the article. In other configurations, each gusset-flap member 19 can extend along at least about 30 percent, and alternatively at least about 40 percent of the longitudinal length 180 of the article to provide improved effectiveness. As illustrated in the representatively shown configurations, each gusset-flap member can extend along a longitudinal length which (as an approximate upper bound) can be up to about 100 percent of the total longitudinal length of the article to provide further gasketing and containment. Alternatively, each gusset-flap member can extend along a length which is not more than about 80 percent, and optionally is not more than about 70 percent of the total longitudinal length of the article to provide desired performance.

Each gusset section 142 of the gusset-flap 19 can be in a bridging configuration across its associated, concave side edge contour 15 of the backsheet layer along a length 182 which is at least about 20 percent of the longitudinal length 180 of the article. In other configurations, each gusset section can be in a bridging configuration across its associated, concave side edge contour 15 of the backsheet layer along a length 182 which is at least about 30 percent, and alternatively is at least about 40 percent of the extent of the longitudinal length 180 of the article to provide improved effectiveness. If desired, each leg gusset section 142 can be in a bridging configuration along a length which can be up to 100 percent of the total longitudinal length of the article to provide further gasketing and containment. Alternatively, each gusset section can be in a bridging configuration along a length which is not more than about 80 percent, and optionally is not more than about 70 percent of the total longitudinal length of the article to provide desired performance and cost effectiveness.

As previously described, each gusset-flap 19 may have an overall longitudinal length which is substantially equal to the overall, total length of the article. Alternatively, each gusset-flap may have a length which is less than the overall, total length of the article, and the relatively shorter gusset-flap may be configured with a zoned-placement at a selected location along an appointed portion of the overall length of the article. Optionally, each gusset-flap 19 may have a total length which is substantially equal to or less than the overall, total length of the absorbent body structure 32, and the relatively shorter containment flap section may be configured with a zoned-placement at a selected location along an appointed portion of the overall length of the absorbent body structure.

To further control the operation of the gusset-flap 19, the arranged array of the gusset elastic members 138 and/or the arranged array of the flap elastic members 68 may be uniformly spaced across the entire width of the leg gusset section 142 and/or containment flap section 144, respectively (as determined along a dimension which is substantially perpendicular to the stretching dimension of the elastic member). Alternatively, the arrangement of the gusset elastics 138 and/or the arrangement of the flap elastics 68 may be grouped into discrete and distinct functional sets. In addition, the multiple, discrete grouping of elastics may be placed in either or both of the leg gusset or containment flap sections of the gusset-flap member 19 to control the operation of the gusset-flap and enhance its performance.

In further aspects of the invention, the elastic members in either or both of the gusset and containment flap sections 142 and 144, respectively, may be operably zone-tensioned. Desirably, the zone tensioning is configured to substantially limit the elasticized gathering to a medial, longitudinally-central section of the gusset-flap member. The zone tensioning may be achieved in a variety of ways. For example, the elastic contractility of the elastic members 138 and 68 in the appropriate end regions of the leg gusset and containment flap sections 142 and 144, respectively, can be operably deadened, such as by a mechanical, ultrasonic or thermal treatment which effectively "kills" or otherwise deactivates the elasticity or contractility in the selected regions.

Alternatively, an adhesive or other bonding mechanism may be applied only in the areas where the retraction of the elastic members is intended to gather the flap composite. In the regions where the bonds are absent, the remaining elastic members can contract substantially without gathering the selected sections of the flap composite. In further configurations, the longitudinally distal end regions of the leg gusset or containment flap sections can be substantially, entirely immobilized, such as by operably securing the end regions onto the topsheet layer 28 (or other part of the article) with adhesive, sonic bonds or other attaching mechanisms.

Typically, the assembled gusset-flap 19 can be attached into the absorbent article 10 while the gusset-flap member 19 is extended to approximately the same extension that was present in the gusset-flap member when as the elastomeric strands 68 and 138 were assembled and attached into the construction of the gusset-flap composite. Accordingly, the gusset-flap member may be attached and incorporated into the article while the fabric and barrier layers of the gusset-flap member are effectively fully extended to their substantially ungathered, flat-out conditions, and the elastomeric strands 68 and 138 are substantially in their initially stretched conditions. Alternatively, the composite, gusset-flap member may be shirred and gathered by a selected amount of elastomeric retraction of the attached elastomeric strands 68 and 138, which is allowed to occur prior to the attaching and incorporating of the composite gusset-flap member 19 into the article 10. The amount of allowed retraction and pre-gathering can be expressed in terms of a percentage based upon the initial, ungathered length of the composite gusset-flap member 19, employing the formula:

$$100*(L_i - L_f)/L_i;$$

where:

$L_i$=the initial, ungathered length of the composite gusset-flap, and $L_f$=the final, gathered length of the composite gusset-flap.

In particular aspects of the invention, the amount of allowed, prior retraction and gathering can be within the range of about 0–50%. The amount of allowed, prior retraction and gathering, in other aspects, can be at least about 10%, and in further aspects, can be not more than about 25% to provide desired benefits and performance. The selected amount of prior or pre-gathering can advantageously help to reduce the amount of gathering force that is initially transmitted to the topsheet and backsheet layers of the article during manufacture, and can help to isolate the topsheet and backsheet layers from the stretching and contracting movements of the gusset-flap member 19 which may occur while article is being worn.

Figure 2:
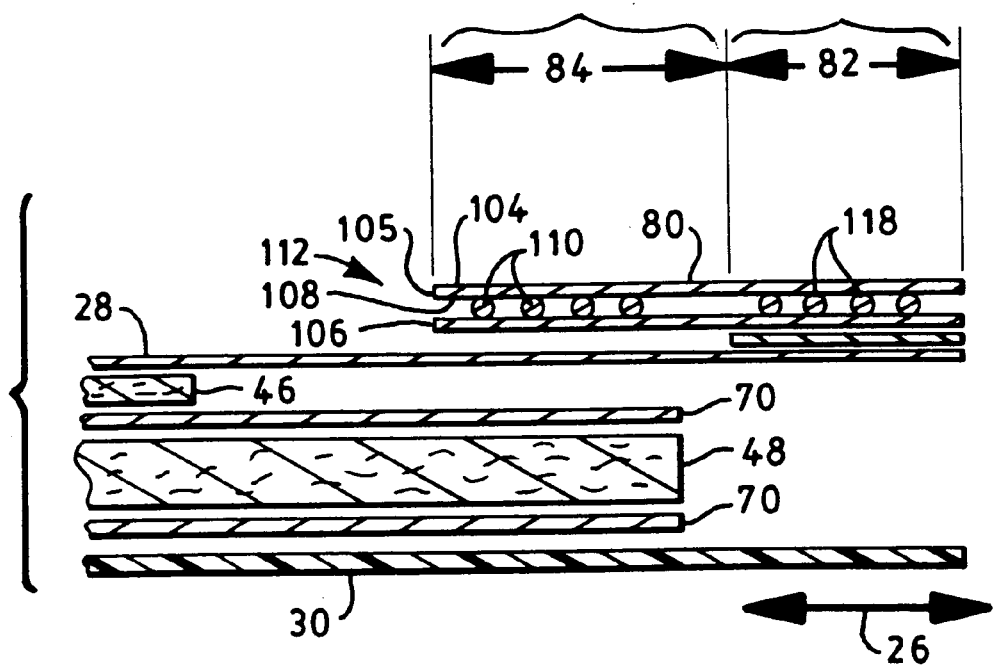
FIG. 2 representatively shows a schematic, expanded cross-sectional view of the waist elastic system and the waist, barrier flap system of the invention taken along a longitudinal centerline of the article when the flap or pocket section is in its flat-out, uncontracted condition.
Figure 3:
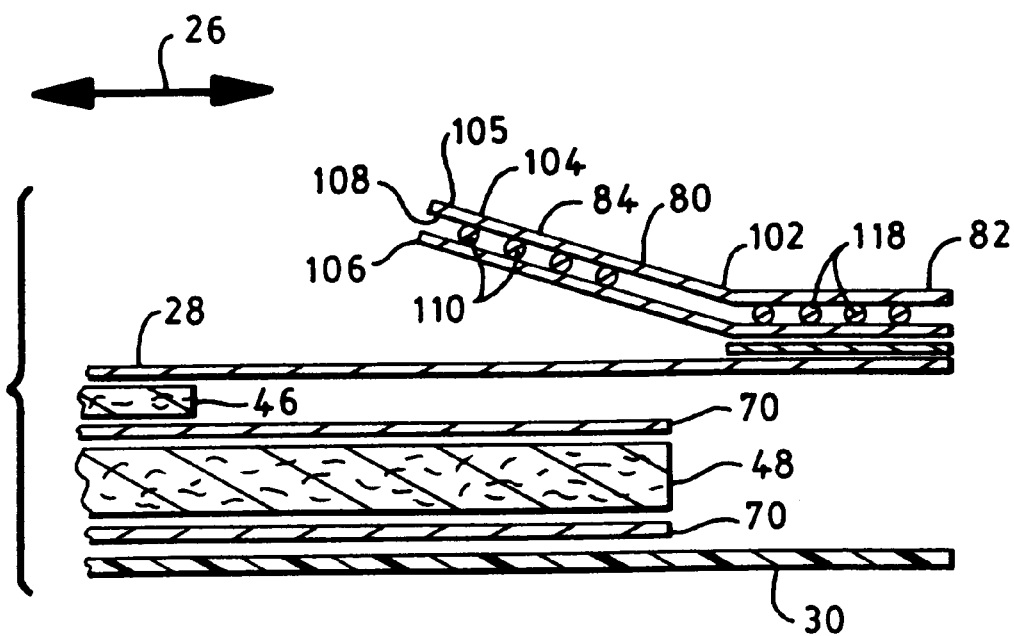
FIG. 3 representatively shows a schematic, expanded cross-sectional view of the waist elastic system and the waist, barrier flap system of the invention taken when the flap or pocket section is in its contracted and opened condition.

With reference to FIGS. 1, 2 and 4, the pocket section 84 of the waist member 80 may be configured to bridge and span over the inward facing, bodyside surfaces of the longitudinally extending containment flap sections 144. Desirably, the movable edge portions 104 of the pocket section 84 are substantially disconnected and unattached to the distal, movable edges 66 of the containment flap sections 144 to thereby reduce interaction between the elasticized containment flap sections 144 and the elasticized pocket section 84. In addition, it can be desirable to zone the elastic tension exerted by the elastic members 68 employed to elasticize the containment flap sections 144. More particularly, the elastic tension in the containment flap sections can be substantially restricted to a longitudinally medial section of each containment flap section. Accordingly, the end regions of each containment flap section, particularly the flap end regions generally adjacent to the pocket section 84, can be substantially free of elastic tension exerted by the elastic members 68. The distal edges 66 can also be secured to the topsheet layer 28 with a suitable attaching mechanism to further isolate the distal edges 66 of the containment flap sections away from the operation and opening of the pocket section 84. Other techniques for producing the desired zoned tensioning of the containment flap sections 144 have been previously described herein.

In particular aspects of the invention, the gusset-flap members 19 can be configured to substantially avoid intersecting the locations of the waist pocket members 80. Accordingly, each of the gusset-flap members can be constructed to terminate at positions which are spaced away from the terminal edges of the pocket sections 84 of the waist pocket members. In other aspects, the gusset-flap members 19 can be configured to lay onto an inwardly facing, bodyside surface of the waist pocket members 80. The gusset-flap members 19 may then terminate in a zone starting from the gatherable moveable edge of the waist pocket 104 to the longitudinal end margin 22 of the absorbent article 10. In yet other aspects, the gusset-flap members 19 can be configured to lay underneath, adjacent an outwardly facing surface of the waist pocket members 80. The gusset-flap members 19 may then terminate in a zone starting from the gatherable moveable edge of the waist pocket 104 to the longitudinal end margin 22 of the absorbent article 10.

In the various arrangements of the invention, the selected absorbent composite system, such as a system which includes the surge management portion 46 and the absorbent body structure 32, is positioned and operably secured between the topsheet 28 and the backsheet 30 to form the diaper 10. The absorbent system has a construction which is generally compressible, conformable, non-irritating to the wearer's skin, and capable of absorbing and retaining liquid body exudates. It should be understood that, for purposes of this invention, any of components of the absorbent system may comprise a single, integral piece of material, or alternatively, may comprise a plurality of individual separate pieces of material which are operably assembled together. Where the absorbent component, such as the absorbent body 32, comprises a single, substantially integral piece of material, the material could include the desired structural features formed into selected spatial regions thereof. Where the absorbent component comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent component. Preferably, each piece is connected to an adjacent portion of the absorbent component by a suitable bonding and/or fiber entanglement mechanism, such as ultrasonic or adhesive bonding, or mechanical or hydraulic needling.

In the representatively shown embodiments, the absorbent body structure 32 has a liquid-acquisition zone, a target zone, and a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions and a central region. The target zone encompasses the area where repeated liquid surges typically occur in absorbent structure 32. When the diaper is worn, the ear regions are configured to generally engage the sides of the wearer's waist and torso, and central region is configured to generally engage the medial portion of the wearers waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied. In a particular aspect of the invention, the absorbent structure has an absorbent capacity of at least about 300 gm of synthetic urine. Alternatively, the absorbent structure can have an absorbent capacity of at least about 400 gm of synthetic urine to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a CAHN, SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-stepwise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled ABSORBENT COMPOSITES AND ABSORBENT ARTICLES CONTAINING SAME and filed on Sep. 11, 1991 (Attorney Docket No. 10,174), the disclosure of which is hereby incorporated by reference in a manner that is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. Pat. No. 5,147,343 of S. Kellenberger, granted Sep. 15, 1992 and entitled ABSORBENT PRODUCTS CONTAINING HYDROGELS WITH ABILITY TO SWELL AGAINST PRESSURE (Attorney Docket No. 8786.1); and also published Nov. 2, 1989 as European Patent Application No. EP 0 339 461 A1; the disclosure of which is hereby incorporated by reference in a manner that is consistent with the present specification.

An example of superabsorbent polymer suitable for use in the present invention is SANWET IM 3900 polymer available from Hoechst Celanese, a business having offices in Portsmouth, Va. Other suitable superabsorbents may include DOW DRYTECH 2035LD polymer obtained from Dow Chemical Co., a business having offices in Midland, Mich.; or FAVOR SAB 870M polymer available from Stockhausen, Inc., a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desirable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–1000 gsm. Again, such basis weight is particularly desirable in the target zone of the absorbent structure. In certain aspects of the invention, the average composite basis weight is within the range of about 500–950 gsm, and preferably is within the range of about 550–900 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 includes 4–22 grams of wood pulp fluff, preferably includes about 8–18 grams of fluff and more preferably includes about 12–14 grams of fluff to provide desired benefits. The wood pulp fluff generally provides shape and form to diaper 10, and carries and positions the particles of superabsorbent polymer or other high-absorbency material. Retention portion 48 can contain about 7–12 grams of superabsorbent polymer, and in the shown embodiment, contains about 8 grams of superabsorbent polymer. Sufficient superabsorbent polymer is incorporated into retention portion 48 to provide an adequate total absorbent capacity of at least about 300 gm of synthetic urine. For example, a medium size diaper for an infant weighing about 16–28 lb (about 7–13 kg) can typically have a total retention capacity of about 400 grams of synthetic urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 3.5–4.5 inches (about 8.9–11.4 cm) in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 to C. Pieper et al., entitled METHOD AND APPARATUS FOR INTERMITTENTLY DEPOSITING PARTICULATE MATERIAL IN A SUBSTRATE and issued Jul. 2, 1991 (Attorney Docket No. 8761), the disclosure of which is hereby incorporated by reference in a manner that is consistent herewith.

In a particular aspect of the invention, absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 9.0 inches (about 22.9 cm), the narrowest portion of the crotch section has a width of about 3.5 inches (about 8.9 cm) and the back waistband region has a width of about 4.5 inches (about 11.4 cm).

The entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as a wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

Absorbent wrap 70 may comprise a multi-element wrap-sheet which includes a separate bodyside wrap layer and a separate outerside wrap layer, each of which extends past all or some of the peripheral edges of retention portion 48, as representatively shown in FIG. 1. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, for example, the bodyside and outerside layers of absorbent wrap 70 extend at least about ½ inch (about 1.3 cm) beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs and facilitate the processibility of the absorbent pad.

To provide the bonding between the bodyside and outerside portions of absorbent wrap 70, an adhesive, such as NATIONAL STARCH 72-3723 adhesive, can be printed onto the appointed bonding areas of the absorbent wrap with, for example, a rotogravure-type system. With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over multiple insults of liquid into the absorbent structure. The addition of a porous, liquid-permeable layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, to transport the liquid from its initial entrance point and to substantially completely release the liquid to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

The representative diaper 10 can include a surge management portion 46 which is arranged in a direct, contacting liquid communication with an adjacent absorbent retention portion 48. As representatively shown, surge management portion 46 may be configured for placement adjacent an outwardly facing, outerside of topsheet 28. Optionally, the surge management portion can be placed adjacent an inwardly facing, bodyside surface of topsheet layer 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

The retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in the target zone, however, the particles can cause the structure to retain and hold unacceptably high amounts of the liquid. In addition, the transport of liquids away from the target zone to other sections of absorbent structure 32, particularly retention portion 48, can be undesirably impaired.

As mentioned previously, surge layer 46 can be a separately formed layer, which lies adjacent the outwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in a generally sideways (X-Y) direction.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately centered about the longitudinal center line of absorbent structure 32, and positioned primarily in a central region of a front section of the absorbent structure 32.

In other aspects of the invention, the end edges of the surge management portion can be spaced longitudinally inboard from the end edges of the retention portion 48. In particular configurations of the invention, the corresponding, relatively adjacent front end edge of surge management portion 46 can be spaced a predetermined discrete distance from a front waistband end edge of the retention portion 48.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. Pat. No. 5,486,166 issued Jan. 23, 1996 to C. Ellis et al., entitled FIBROUS NONWOVEN WEB SURGE LAYER FOR PERSONAL CARE ABSORBENT ARTICLES AND THE LIKE, (attorney docket No. 11,256); and U.S. Pat. No. 5,490,846 granted Feb. 13, 1996 to C. Ellis et al., entitled IMPROVED SURGE MANAGEMENT FIBROUS NONWOVEN WEB FOR PERSONAL CARE ABSORBENT ARTICLES AND THE LIKE, (attorney docket No. 11,387); the disclosures of which are hereby incorporated by reference in a manner that is consistent herewith.

In desired configurations of the invention, the surge material can include natural fibers, synthetic fibers, such as synthetic polymer fibers, and combinations thereof. The fabric can, for example, be composed of polyolefin fibers, and in particular configurations the fibers can include bicomponent fibers. For example, polypropylene/polyethylene bicomponent fibers may be employed to form the bicomponent fiber portion of any of the described fabrics. In addition, the bicomponent fibers may be flat crimped or helically crimped.

In the shown configuration of the article, the side panel members 56 are separately provided members which are operably connected and attached to laterally opposed end sections of the back waistband portion of backsheet 30. In particular, each side panel is affixed to extend away from a corresponding terminal edge of the backsheet layer. The side panels can be composed of a substantially non-elastomeric material, such as polymer films, woven fabrics, nonwoven fabrics or the like, as well as combinations thereof. In particular aspects of the invention, the side panels are composed of an elasticized material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application No. EP 0 110 010 published on Apr. 8, 1987 as EP 0 217 032 A2 with the inventors listed as J. Taylor et al., the disclosure of which is hereby incorporated by reference. Examples of NBL materials are described in U.S. Pat. No. 5,226,992 issued Jul. 13, 1993 to M. Mormon, the disclosure of which is hereby incorporated by reference.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (attorney docket No. 11,186); in U.S. Pat. No. 5,540,796 which issued Jul. 30, 1996 to D. Fries, entitled A PROCESS FOR ASSEMBLING ELASTICIZED EAR PORTIONS, (attorney docket No. 11,169); in U.S. Pat. No. 5,595,618 which issued Jan. 21, 1997 to D. Fries, entitled AN ASSEMBLY PROCESS FOR A LAMINATED TAPE, (attorney docket No. 11,950); and in U.S. Pat. No. 5,549,592 which issued Aug. 27, 1996 to D. Fries, entitled AN ABSORBENT ARTICLE WITH A LAMINATED TAPE, (attorney docket No. 11,990). The entireties of the disclosures of the above-described documents are incorporated herein by reference in a manner that is consistent (not in conflict) herewith.

The fastener system can optionally include a separately provided reinforcement strip which is composed of a strengthening and/or stiffening material, and is laminated to an appointed first surface of each of the side panel members 56 at the outboard region of the side panel. The shown reinforcement strip extends along substantially the entire length of the outboard end portion of the panel member 56. In addition, the reinforcement strip has a length which is greater than the length dimension of the securing mechanism 44 on the user-bond portion 38 of the fastener tab 36. The reinforcement strip can, for example, be composed of a release tape, and the release tape can include a substrate composed of a polymer film, such as a polypropylene film. Suitable release tape materials are available from Avery Corp., a business having offices located in Painesville, Ohio.

In particular, the reinforcement strip can be operably bonded and laminated to the outboard region of the panel member 56 along the first surface of the panel member. The shown reinforcement strip can be configured with its terminal outboard edge positioned substantially coterminous and substantially coextensive with the outboard edge of the panel member 56. In addition, the width of the release tape along the cross-direction 24 is desirably equal to or greater than the width of the securing mechanism 44 provided on the user-bond region 38 of the fastener tab 36.

The illustrated fastening system includes a complementary, opposed pair of fastener tabs 36, which provide a mechanism for holding the article on the wearer. Each of the fastener tabs includes a tab substrate 86, which may be composed of various substrate materials. For example, the shown embodiment of the tab substrate can be composed of a polymer film, such as a polypropylene film. Suitable film materials are available from Avery Corp., a business having offices located in Painesville, Ohio. Alternatively, the securement web may include a woven or nonwoven fabric, such as spunbond nonwoven fabric.

The representatively shown tab substrate 86 includes an appointed securement surface and an opposed user surface, and includes a selected securing means which is positioned onto the securement surface of the tab substrate. The securing means may be provided by an adhesive, a cohesive material, a cooperating component of a interengaging, mechanical fastener, snaps, pins or buckles and the like, as well as combinations thereof. For example, the securing means may include a hook (e.g. mushroom-head) component or a loop component of a hook-and-loop fastener. In the shown configuration, the securing means is provided by a layer of primary adhesive distributed over the appointed securing surface, and the fastening system provides an adhesive fastener tab. The fastener tabs can be constructed to releasably adhere to an appointed landing zone patch 92 which is attached to the front waistband section of the diaper to provide an adhesive or mechanical fastening system which is refastenable.

With the adhesive securing means, the layer of primary adhesive can be employed to operably laminate and affix the appointed factory-bond region 39 of the fastener tab 36 to the outboard region of the panel member 56 along an appointed second surface of the panel member. Other types of connecting means, such as thermal bonds, sonic bonds, mechanical stitching, stapling and the like, as well as combinations thereof, may alternatively be employed to permanently attach the fastener tab to the panel member.

For example, ultrasonic bonds may be employed to provide a selected supplemental bonding.

With reference to FIG. 1, the fastener tab 36 includes a factory-bond section 39 which overlaps the outboard edge of the panel member 56, and extends beyond the panel member to provide the user-bond region of the fastener tab. In particular arrangements of the invention, the fastener tab can have a relatively wide user-bond section in combination with a relatively narrower intermediate section. The intermediate section is positioned between the user-bond and factory-bond sections of the fastener tab. In a further aspect of the invention, the fastener tab 36 may optionally include a finger tab region. The finger tab can be substantially non-securing, and can provide an area that can be readily grasped by the user without contaminating or otherwise adversely affecting the securing means.

Various types and arrangements of interengaging mechanical securing means can be employed to provide an operable fastening system for the various configurations of the invention. Representative examples of suitable mechanical fastener configurations are described in U.S. Pat. No. 5,605,735 which issued Feb. 25, 1997 to G. Zehner et al., entitled HIGH-PEEL TAB FASTENER, (attorney docket No. 11, 571); and in U.S. patent application Ser. No. 421,640 by P. VanGompel et al., entitled MULTI-ATTACHMENT FASTENING SYSTEM and filed Apr. 13, 1995 (attorney docket No. 11,430), the entire disclosures of which are hereby incorporated by reference in a manner that is consistent herewith.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a longitudinal length dimension, a lateral cross dimension, a front waistband portion, a back waistband portion, and an intermediate portion which interconnects said front and back waistband portions, said article comprising:

a backsheet layer having a pair of laterally opposed and longitudinally extending side margins, each side margin having an outwardly concave, terminal side edge contour located at appointed leg opening regions in an intermediate portion of said each side margin, each concave side edge contour having a selected longitudinal extent along said length dimension of said article;

a liquid permeable topsheet layer connected in a superposed facing relation to said backsheet layer;

an absorbent body sandwiched between said topsheet layer and said backsheet layer; and a separately provided gusset-flap composite member connected to at least one of said backsheet and topsheet layers along each of said leg opening regions, said gusset-flap member providing a leg gusset section and a containment flap section; wherein each leg gusset section is configured to extend beyond and bridge across its corresponding, outwardly concave terminal side edge contour of said backsheet layer, and to provide an elasticized and gathered side margin of said article;

each containment flap section is integrally formed with a corresponding one of said leg gusset sections and positioned relatively inboard therefrom to provide said gusset-flap member;

each containment flap section has a substantially fixed edge located proximally adjacent to a one of said elasticized side margins, and has an elasticized and gathered, distal, movable edge portion; and wherein said gusset-flap member includes a barrier layer having a pair of laterally opposed, longitudinally extending, barrier layer side edges, and first and second major facing surfaces, a fabric layer which is joined in facing relation with said first facing surface of said barrier layer, said fabric layer having a leg gusset region, an outboard side portion, a containment flap region, and an inboard side portion, said outboard side portion arranged to wrap around at least one side edge of said barrier layer and extend inboard therefrom along said second facing surface of said barrier layer, a first arrangement of a first plurality of separate, longitudinally extending elastomeric members attached and sandwiched by said barrier layer and said fabric layer within said leg gusset section of said gusset-flap member, and a second arrangement of at least one longitudinally extending elastomeric member attached to at least said fabric layer within each containment flap section of said gusset-flap member, said first and second arrangements of elastomeric members thereby providing an elastomeric, substantially longitudinally gathered, gusset-flap composite.

2. An article as recited in claim 1, wherein said inboard side portion of said fabric layer is arranged to wrap around to sandwich said second arrangement of at least one longitudinally extending elastomeric member.

3. An article as recited in claim 1, wherein said inboard side portion of said fabric layer is arranged to wrap around a second side edge of said barrier layer, and said at least one longitudinally extending elastomeric member attached between said fabric layer and said barrier layer within said containment flap section of said each gusset-flap member.

4. An article as recited in claim 1, wherein said first arrangement of elastomeric members includes a first set of laterally spaced-apart elastomeric members joined to said first major surface of said barrier layer and a second set of laterally spaced-apart elastomeric members joined to said second major surface of said barrier layer.

5. An article as recited in claim 4, wherein said first set of elastomeric members are laterally offset and staggered with respect to said second set of elastomeric members.

6. An article as recited in claim 1, wherein
said barrier layer extends into the containment flap section of said gusset-flap member, and
said second arrangement of at least one elastomeric member includes a second plurality of elastomeric members, with a first set of laterally spaced-apart elastomeric members joined to said first major surface of said barrier layer and a second set of laterally spaced-apart elastomeric members joined to said second major surface of said barrier layer.

7. An article as recited in claim 6, wherein said barrier layer and fabric layer are substantially unattached to each other at intermediate regions located between immediately adjacent members of said second plurality of elastomeric members.

8. An article as recited in claim 1, wherein said barrier layer and fabric layer are substantially unattached to each other at intermediate regions located between immediately adjacent members of said first plurality of elastomeric members.

9. An article as recited in claim 8, wherein each of said first plurality of elastomeric members is attached to at least one of said gusset-flap barrier and fabric layers with a substantially separate strip of adhesive.

10. An article as recited in claim 8, wherein each of said second plurality of elastomeric members is attached to at least one of said gusset-flap barrier and fabric layers with a substantially separate strip of adhesive.

11. An article as recited in claim 1, wherein each leg gusset section is connected to a bodyside surface of said topsheet layer, each of said outwardly concave, terminal side edge contours has a longitudinal length which extends along at least about 20% of a total longitudinal length of said article, and each leg gusset section is in a bridging configuration across at least about 20% of a total length of the backsheet layer.

12. An article as recited in claim 1, wherein each of said backsheet side margins generally defines a plane thereof; and each of said leg gusset sections is constructed to extend beyond its associated concave side edge contour of said backsheet layer in an arrangement which lies substantially within the plane of its associated backsheet side margin.

13. An article as recited in claim 1, wherein each said leg gusset section has a composite stiffness of not less than about 5 mg.

14. An article as recited in claim 13, wherein each said leg gusset section provides a member having a composite stiffness of not more than about 250 mg.

15. An article as recited in claim 1, wherein each leg gusset section has a lateral width of not less than about 13 mm.

16. An article as recited in claim 1, wherein each leg gusset section is connected to said article with a gusset attachment for holding said leg gusset substantially parallel to said plane of its associated backsheet side margin.

17. An article as recited in claim 16, wherein said gusset-flap attachment includes an article edge attachment which secures said leg gusset to said article adjacent to its associated, outwardly concave terminal side edge contour of said backsheet layer along substantially an entire length of said side edge contour within which said leg gusset and said side edge contour are coextensive.

18. An article as recited in claim 13, wherein each containment flap section has a composite stiffness of not less than about 10 mg.

19. An article as recited in claim 18, wherein each containment flap section has a composite stiffness of not more than about 250 mg.

20. An article as recited in claim 1, wherein at least a portion each leg gusset section extends laterally beyond its corresponding, outwardly concave terminal side edge contour of said backsheet layer at its narrowest point in the crotch area by a distance of not less than about 3 mm.

21. An article as recited in claim 1, wherein said barrier layer and fabric layer have a reduced adhesive amount at intermediate areas which are located between immediately adjacent members of said first plurality of elastomeric members, as compared to an adhesive amount located at the positions of said first plurality of elastomeric members.

22. An article as recited in claim 4, wherein said barrier layer and fabric layer have a reduced adhesive amount at intermediate areas which are located between immediately adjacent members of said first plurality of elastomeric members, as compared to an adhesive amount located at the positions of said first plurality of elastomeric members.

23. An article as recited in claim 1, wherein said second arrangement of at least one elastomeric member is attached to at least one of said gusset-flap barrier and fabric layers with an increased amount of adhesive, as compared to an amount of adhesive located in said boundary space between said first arrangement of elastomeric members and said second arrangement of at least one elastomeric member.

24. An article as recited in claim 6, wherein each of said second plurality of elastomeric members is laminated to at least one of said gusset-flap barrier and fabric layers with an increased amount of adhesive, as compared to an amount of adhesive located at intermediate regions which positioned between immediately adjacent members of said second plurality of elastomeric members.

25. An article as recited in claim 1, wherein each said gusset-flap member has been gathered by a selected amount prior to incorporating said each gusset-flap member into said article.

* * * * *